(12) United States Patent
Akimoto et al.

(10) Patent No.: US 9,805,879 B2
(45) Date of Patent: Oct. 31, 2017

(54) DYE-SENSITIZED SOLAR CELL

(71) Applicant: ADEKA CORPORATION, Tokyo (JP)

(72) Inventors: Kensaku Akimoto, Tokyo (JP); Toru Yano, Tokyo (JP); Koichi Sakamaki, Tokyo (JP)

(73) Assignee: ADEKA CORPORATION, Tokyo (JP)

(*) Notice: Subject to any disclaimer, the term of this patent is extended or adjusted under 35 U.S.C. 154(b) by 403 days.

(21) Appl. No.: 14/353,661

(22) PCT Filed: Nov. 27, 2012

(86) PCT No.: PCT/JP2012/080606
§ 371 (c)(1),
(2) Date: Apr. 23, 2014

(87) PCT Pub. No.: WO2013/099492
PCT Pub. Date: Jul. 4, 2013

(65) Prior Publication Data
US 2014/0299191 A1    Oct. 9, 2014

(30) Foreign Application Priority Data
Dec. 28, 2011    (JP) .................................. 2011-288918

(51) Int. Cl.
*H01G 9/20* (2006.01)
*H01L 51/00* (2006.01)
(Continued)

(52) U.S. Cl.
CPC ........... *H01G 9/204* (2013.01); *C07F 7/1836* (2013.01); *C07F 15/0053* (2013.01);
(Continued)

(58) Field of Classification Search
CPC .... H01G 9/2059; H01G 9/2031; H01G 9/204; C07F 15/0053; C07F 17/02;
(Continued)

(56) References Cited

U.S. PATENT DOCUMENTS

2009/0293951 A1    12/2009  Moon et al.

FOREIGN PATENT DOCUMENTS

CN    101275037    10/2008
CN    101294004    10/2008
(Continued)

OTHER PUBLICATIONS

Extended European Search Report—PCT/JP2012/080606—dated Oct. 2, 2015.
(Continued)

*Primary Examiner* — Matthew T Martin
(74) *Attorney, Agent, or Firm* — Young & Thomspon

(57) ABSTRACT

A dye-sensitized solar cell including a working electrode having a photocatalytic film, a counter electrode, and an electrolyte-containing layer or solid charge-transfer layer containing a basic compound, wherein the photocatalytic film includes an oxide semiconductor layer containing a dye compound represented by the following formula (1),

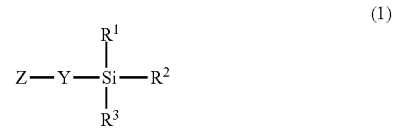

wherein Y is an optionally substituted hydrocarbon group having 1 to 20 carbon atoms and having —CO—NR$^4$— or —SO$_2$—NR$^4$— in the group, or a direct bond, Z is a conjugated group, R$^1$, R$^2$, and R$^3$ each represent an optionally substituted hydrocarbon group or an optionally substituted hydrocarbonoxy group, at least one of R$^1$, R$^2$, and R$^3$ is an optionally substituted hydrocarbonoxy group, and R$^4$ represents a hydrogen
(Continued)

atom or an optionally substituted hydrocarbon group having 1 to 20 carbon atoms.

20 Claims, 2 Drawing Sheets

(51) Int. Cl.
 C09B 69/00 (2006.01)
 C07F 15/00 (2006.01)
 C07F 17/02 (2006.01)
 C07F 7/18 (2006.01)
(52) U.S. Cl.
 CPC ............ C07F 17/02 (2013.01); C09B 69/008 (2013.01); H01G 9/2031 (2013.01); H01G 9/2059 (2013.01); H01L 51/0064 (2013.01); H01L 51/0094 (2013.01); H01L 51/0086 (2013.01); H01L 51/0091 (2013.01); H01L 51/0092 (2013.01); Y02E 10/542 (2013.01); Y02E 10/549 (2013.01)
(58) Field of Classification Search
 CPC .... C07F 7/1863; Y02E 10/549; Y02E 10/542; C09B 69/008
 See application file for complete search history.

(56) References Cited

FOREIGN PATENT DOCUMENTS

| EP | 2 386 607 | 11/2011 |
|---|---|---|
| JP | 2002-075474 | 3/2002 |
| JP | 2008-063390 | 3/2008 |
| JP | 2010-027749 | 2/2010 |
| JP | 2011-026412 | 2/2011 |

OTHER PUBLICATIONS

Baik C et al: "Organic dyes with a novel anchoring group for dye-sensitive solar cell applications", Journal of Photochemistry and Photobiology, A: Chemistry, Elsevier Sequoia, Lausanne, CH, vol. 201, No. 2-3, Jan. 25, 2009 (Jan. 25, 2009), pp. 168-174, XP025860108, ISSN: 1010-6030, DOI: 10.1016/J.JPHOTOCHEM. 2008.10.018 [retrieved on Nov. 6, 2008] p. 169; figure 1, abstract.
Xing Fan et al., "Conductive mesh based flexible dye-sensitized solar cells", Applied Physics Letters, 90, 073501 (2007).
Yoshikazu Yoshida et al., "Transparent conductive oxide layer-less dye sensitized solar cells consisting of floating electrode with gradient TiOx blocking layer", Applied Physics Letters, 94, 093301 (2009).
International Search Report, PCT/JP2012/080606, dated Jan. 8, 2013.
Zhou YF, "Performances improvement of eosin y sensitized solar cells by modifying Ti02 electrode with silane-coupling reagent" Chinese Science Bulletin (2009), 54 (15), 2633-40.
Kakiage K, "High Performance of Si—O—Ti Bonds for Anchoring Sensitizing Dyes on Ti02 Elecrodes in Dye-sensitized Solar Cells Evidenced by Using Alkoxysilylazobenzenes" Chemistry Letters (2010), 39 (3), 260-262.

DYE-SENSITIZED SOLAR CELL

TECHNICAL FIELD

The present invention relates to a dye-sensitized solar cell containing a basic compound in an electrolyte-containing layer or a solid charge-transfer layer, wherein an oxide semiconductor layer containing a sensitizing dye having a specific structure is used.

BACKGROUND ART

Dye-sensitized solar cells are being researched and developed actively as next generation solar cells that can substitute for silicon-based solar cells, because dye-sensitized solar cells have excellent advantages. Such advantages are as follows: (1) they are expected to need production costs as low as $1/5$ to $1/10$ of those of silicon-based solar cells and therefore they are inexpensive, (2) the amount of $CO_2$ emitted during their production is as small as $1/10$ or less of that with single crystal silicon solar cells, (3) the energy payback time or the $CO_2$ payback time thereof is as short as half or less of those of polycrystalline silicon solar cells, (4) there are fewer constraints with respect to resources of their raw materials, (5) they excel in aesthetic properties and processability and therefore larger-sized ones can be manufactured easily, and (6) they have relatively high photoelectric conversion efficiencies as high as 10% or more, which are comparable to those of amorphous silicon solar cells.

FIG. 1, FIG. 3, and FIG. 4 each shows schematically the sectional configuration of an example of the conventional dye-sensitized solar cells. FIG. 2 extracts and enlarges a principal part of the dye-sensitized solar cell represented in FIG. 1. The dye-sensitized solar cell represented in FIG. 1 is a product in which a working electrode 10 and a counter electrode 20 are opposed to each other via an electrolyte-containing layer 30. At least one of the working electrode 10 and the counter electrodes 20 is a light-transmissive electrode. The working electrode 10 has a substrate 11A on which a conductive layer 11B and a metal oxide semiconductor layer 12 are laminated together. The dye-sensitized solar cells depicted in FIG. 3 and FIG. 4 are of interest because they can be produced at low cost since the conductive layer 11B needs not be transparent if the substrate 11A is transparent. When the configuration of FIG. 3 or FIG. 4 is adopted, the conductive layer 11B to be used need to be porous or lattice-like one through which electrolyte components can pass (Non-Patent Literatures 1 and 2).

As shown in FIG. 1 and FIG. 2, a dye-sensitized solar cell is composed of a working electrode (photoelectric conversion device) 10, a counter electrode 20, and an electrolyte-containing layer (electrolytic solution) 30 sandwiched between the two electrodes. The working electrode 10 is prepared by following procedure. First, nanosized metal oxide semiconductor particles 12B are applied to a surface of a substrate 11A such as glass on the conductive layer side on which a conductive layer 11B is formed. Next, the metal oxide semiconductor particles 12B are baked to form a metal oxide semiconductor layer 12. Then, a dye 13 is fixed to the metal oxide semiconductor particles 12B by chemical/physical adsorption. The counter electrode 20 is a product in which a conductive layer 22 is formed on a surface of a substrate 21 such as glass. The counter electrode 20 is prepared by applying platinum treatment or conductive carbon treatment in a catalytic amount to the conductive layer side of the substrate 21. The solar cell is prepared by superposing the working electrode 10 and the counter electrode 20 and then injecting the electrolyte composition containing an iodine compound (electrolyte-containing layer 30) to between the electrodes 10 and 20.

In the power generation mechanism of a dye-sensitized solar cell, electrons are injected from a sensitizing dye excited by solar light (visible light) irradiation into a conduction band of a metal oxide semiconductor. The injected electrons are introduced into an external circuit through a photoelectrode and then move to a counter electrode and then, via a redox reaction of an electrolyte composition, the sensitizing dye (dye cation) in an oxidized state receives electrons to regenerate. Photoelectric conversion is attained by this cycle.

Because of a lower photoelectric conversion efficiency as compared with the commercially available silicon-based solar cells, dye-sensitized solar cells are not in industrial use. The main factor of the drop of photoelectric conversion efficiency of a dye-sensitized solar cell lies in the drop of voltage caused by reverse electron transfer from an oxide semiconductor layer to an electrolyte composition and a dye cation and therefore addition of a basic compound to an electrolyte composition has been investigated in order to inhibit reverse electron transfer to prevent voltage drop.

The addition of a basic compound inhibits reverse electron transfer, but it has a problem that the sensitizing dye adsorbed on the metal oxide semiconductor is desorbed easily. Thus, there have been attempts at inhibiting the desorption from a metal oxide by making a sensitizing dye have an anchor group such as a carboxyl group and a silanol group (Patent Literature 1 to 3).

CITATION LIST

Patent Literature

Patent Literature 1: JP 2008-063390 A
Patent Literature 2: JP 2010-027749 A
Patent Literature 3: JP 2011-026412 A

Non-Patent Literature

Non-Patent Literature 1: X. al. Appl. Phys. Lett., 90, 073501 (2007)
Non-Patent Literature 2: Y. Yoshida, et. al., Appl. Phys. Lett., 94, 093301 (2009)

SUMMARY OF INVENTION

Technical Problem

Therefore, the object of the present invention is to provide a dye-sensitized solar cell in which desorption of a sensitizing dye can be suppressed even when an electrolyte-containing layer or a solid charge transfer layer containing a basic compound is used.

Solution to Problem

As a result of earnest study, the inventors have found a combination of a dye compound having a specific structure and a basic compound. Then, the inventors have completed the present invention based on the finding that the object can be achieved with such a combination.

That is, the present invention provides a dye-sensitized solar cell comprising a working electrode having a photocatalytic film, a counter electrode, and an electrolyte-containing layer or a solid charge-transfer layer, wherein the dye-sensitized solar cell contains a basic compound in the electrolyte-containing layer or the solid charge transfer layer, and the photocatalytic film comprises an oxide semiconductor layer containing a dye compound represented by the following formula (1),

[Chemical Formula 1]

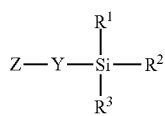

(1)

wherein Y is an optionally substituted hydrocarbon group having 1 to 20 carbon atoms and having —CO—NR$^4$— or —SO$_2$—NR$^4$— in the group, or a direct bond, Z is a conjugated group; R$^1$, R$^2$, and R$^3$ each represent an optionally substituted hydrocarbon group or an optionally substituted hydrocarbonoxy group; at least one of R$^1$, R$^2$, and R$^3$ is an optionally substituted hydrocarbonoxy group; and R$^4$ represents a hydrogen atom or an optionally substituted hydrocarbon group having 1 to 20 carbon atoms.

Effect of Invention

The dye-sensitized solar cell of the present invention is excellent in adsorption onto a metal oxide semiconductor even in the case that the electrolyte-containing layer or the solid charge-transfer layer contains a basic compound because the sensitizing dye has a silyl group in which a hydrocarbonoxy group and a Si atom are linked. In addition, because of the high adsorption, the dye-sensitized solar cell of the present invention is a device with high efficiency and high durability.

DESCRIPTION OF EMBODIMENTS

Figure 3:
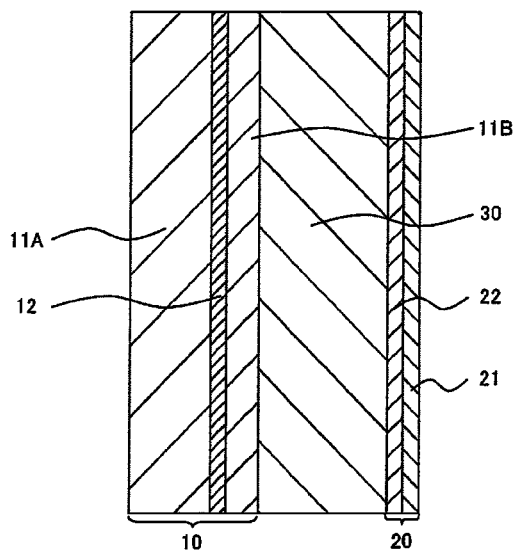
FIG. 3 is a schematic diagram showing a cross-sectional configuration in another example of the conventional dye-sensitized solar cells.
Figure 4:
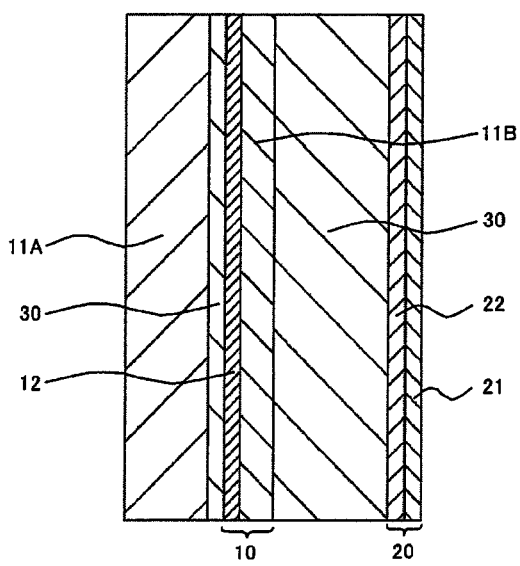
FIG. 4 is a schematic diagram showing a cross-sectional configuration in still another example of the conventional dye-sensitized solar cells.

Hereinafter, the dye-sensitized solar cell of the present invention will be described with reference to preferred embodiments. The configuration of the dye-sensitized solar cell of the present invention is not particularly limited as long as the cell has a working electrode having a photocatalytic film, a counter electrode, and an electrolyte-containing layer, and specific examples can be those with the configurations depicted in FIG. 1, FIG. 3, and FIG. 4.

When the dye 13 supported on the working electrode 10 in this dye-sensitized solar cell is irradiated with light (sunlight, or ultraviolet light, visible light, or near infrared light equivalent to sunlight), the dye 13 is excited by absorbing the light to inject electrons into the metal oxide semiconductor layer 12. The electrons are transferred to the adjacent conductive layer 11B and then reach the counter electrode 20 via the external circuit. On the other hand, in the electrolyte-containing layer 30, the electrolyte is oxidized so that the dye 13 which has been oxidized with the electron transfer can return (or be reduced) to its ground state. The oxidized electrolyte is reduced by receiving electrons that have reached the counter electrode 20. Thus, the electrons transfer between the working electrode 10 and the counter electrode 20 and the associated redox reaction in the electrolyte-containing layer 30 are repeated. This generates continuous transfer of electrons to enable steady photoelectric conversion.

Description will be made to the working electrode 10. For example, the working electrode 10 includes a conductive substrate 11, a metal oxide semiconductor layer 12 provided on one surface (the counter electrode 20-side surface) of the substrate 11, and a dye 13 supported on the metal oxide semiconductor layer 12. In the dye-sensitized solar cell of the present invention, the dye 13 is a compound represented by the above formula (1).

The working electrode 10 functions as a negative electrode for the external circuit. For example, the conductive substrate 11 includes an insulating substrate 11A and a conductive layer 11B provided on the surface of the substrate 11A.

For example, the substrate 11A may be made of an insulating material such as glass or plastic. For example, plastic is used in the form of a transparent polymer film. Examples of plastic used to form a transparent polymer film include tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyestersulfone (PES), polyetherimide (PEI), cyclic polyolefin, brominated phenoxy resin, or the like.

Examples of the conductive layer 11B include a conductive metal oxide thin film including indium oxide, tin oxide, indium-tin complex oxide (ITO), fluorine-doped tin oxide (FTO: F—SnO$_2$), or the like; a metal thin film including gold (Au), silver (Ag), platinum (Pt), or the like; and a layer made of a metal mesh, a conductive polymer, or the like.

Alternatively, for example, the conductive substrate 11 may be a monolayer structure made of a conductive material. In this case, the conductive substrate 11 is typically made of a conductive metal oxide such as indium oxide, tin oxide, indium-tin complex oxide, or fluorine-doped tin oxide, a metal such as gold, silver, or platinum, or a conductive polymer.

Figure 2:
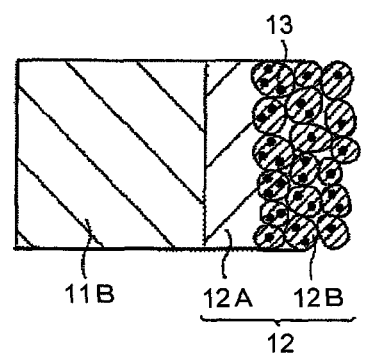
FIG. 2 is an enlarged diagram of the principal part of the dye-sensitized solar cell depicted in FIG. 1.

The metal oxide semiconductor layer 12 is a support, on which the dye 13 is supported, and, for example, has a porous structure as shown in FIG. 2. The metal oxide semiconductor layer 12 includes a dense layer 12A and a porous layer 12B. The dense layer 12A, which is formed at the interface with the conductive substrate 11, is preferably dense and less-porous, more preferably in the form of a film. The porous layer 12B, which is formed at the surface in contact with the electrolyte-containing layer 30, preferably has a structure with a large number of pores and a large surface area, and more preferably a porous structure made of deposited fine particles. Alternatively, for example, the metal oxide semiconductor layer 12 may be formed to have a film-shaped monolayer structure. In this description, the term "carrying" or "supported on" refers to a state in which the dye 13 is chemically, physically, or electrically bonded or adsorbed to the porous layer 12B.

The material (metal oxide semiconductor material) that constitutes the metal oxide semiconductor layer 12 may be, for example, titanium oxide, zinc oxide, tin oxide, niobium oxide, indium oxide, zirconium oxide, tantalum oxide, vanadium oxide, yttrium oxide, aluminum oxide, or magnesium oxide. Titanium oxide and zinc oxide are particularly preferred as the metal oxide semiconductor material in that they can yield high conversion efficiency. Any of these metal oxide semiconductor materials may be used alone or in combination of two or more (as a mixture, a mixed crystal, a solid solution, a surface coating, or the like). For example, titanium oxide may be used in combination with zinc oxide or the like.

The metal oxide semiconductor layer 12 having a porous structure may be formed using a method such as an electrolytic deposition technique, a coating technique, or a firing technique. A process of forming the metal oxide semiconductor layer 12 using an electrolytic deposition technique may include providing an electrolytic bath liquid containing fine particles of a metal oxide semiconductor material and depositing the fine particles on the conductive layer 11B of the conductive substrate 11 in the electrolytic bath liquid so that the metal oxide semiconductor material is precipitated thereon. A process of forming the metal oxide semiconductor layer 12 using a coating technique may include applying, to the conductive substrate 11, a dispersion (metal oxide slurry) containing dispersed fine particles of a metal oxide semiconductor material, and then drying the applied dispersion to remove the dispersion medium from the dispersion. A process of forming the metal oxide semiconductor layer 12 using a firing technique may include applying a metal oxide slurry to the conductive substrate 11 in the same way as in the coating technique, drying the slurry, and then firing the dried material. Especially when an electrolytic deposition technique or a coating technique is used to form the metal oxide semiconductor layer 12, a less heat-resistant plastic material or polymer film material can be used as the substrate 11A, so that a highly flexible electrode can be formed.

The metal oxide semiconductor layer 12 may also be treated with an organic base, a urea derivative, or a cyclic sugar chain. Examples of the organic base include diarylamine, triarylamine, pyridine, 4-tert-butylpyridine, polyvinyl pyridine, quinoline, piperidine, and amidine. The treatment may be performed before or after the dye 13 is adsorbed as described below. The treatment method may be an immersion treatment. A solid treatment agent may be dissolved in an organic solvent and then be used for the immersion treatment.

The dye 13, for example, is adsorbed to the metal oxide semiconductor layer 12. The dye 13 includes one or more dyes (sensitizing dyes) capable of injecting electrons into the metal oxide semiconductor layer 12 when excited by absorbing light. In the dye-sensitized solar cell of the invention, the compound represented by the above formula (1) corresponds to the dye 13. The use of the compound represented by the above formula (1) as the dye 13 suppresses the dye 13 to be desorbed even if a basic compound is contained in an electrolyte-containing layer 30, which is described later.

The compound represented by the above formula (1) to be used as the dye 13 is described below.

The group represented by Y in formula (1) is a divalent group and specifically is a direct bond or an optionally substituted hydrocarbon group having 1 to 20 carbon atoms and having —CO—NR$^4$— or —SO$_2$—NR$^4$—. Examples of the optionally substituted hydrocarbon group include an aliphatic hydrocarbon group, an unsubstituted aromatic hydrocarbon group, an aromatic hydrocarbon group substituted with an aliphatic hydrocarbon group, an unsubstituted heterocyclic group, or a heterocyclic group substituted by an aliphatic hydrocarbon group.

Examples of the divalent aliphatic hydrocarbon group include linear, branched, or cyclic aliphatic hydrocarbon groups and specifically include methane-1,1-diyl, ethane-1,2-diyl, 1-methylethane-1,2-diyl, propane-1,3-diyl, butane-1,4-diyl, 2-methylpropane-1,3-diyl, pentane-1,5-diyl, hexane-1,6-diyl, heptane-1,7-diyl, octane-1,8-diyl, nonane-1,9-diyl, decane-1,10-diyl, cyclohexane-1,4-diyl, or the like. Especially, methane-1,1-diyl, ethane-1,2-diyl, and 1-methylethane-1,2-diyl are preferred because they will enhance the conversion efficiency of the working electrode (photoelectric conversion device) 10.

Examples of the divalent unsubstituted aromatic hydrocarbon group include 1,2-phenylene, 1,3-phenylene, 1,4-phenylene, or the like.

Examples of the divalent unsubstituted heterocyclic group include furan-2,5-diyl, furan-3,5-diyl, thiophene-2,5-diyl, thiophene-3,5-diyl, 2H-chromene-3,7-diyl, benzothiophene-2,6-diyl, benzothiophene-2,5-diyl, or the like.

Examples of the divalent aromatic hydrocarbon group substituted with an aliphatic hydrocarbon group include groups having one to three aliphatic hydrocarbon groups of 1 to 4 carbon atoms as substituents on the divalent unsubstituted aromatic hydrocarbon group described above. Examples of the divalent heterocyclic group substituted with an aliphatic hydrocarbon group include groups having one to three aliphatic hydrocarbon groups of 1 to 4 carbon atoms as substituents on the divalent unsubstituted heterocyclic group described above. Examples of the aliphatic hydrocarbon group having 1 to 4 carbon atoms include linear, branched, or cyclic alkyl groups, such as methyl, ethyl, propyl, isopropyl, butyl, sec-butyl, tert-butyl, isobutyl, cyclopropyl, and cyclobutyl, and the aliphatic hydrocarbon group having 1 to 4 carbon atoms may be interrupted by —O—, —COO—, —COO—, —CO—, —S—, —SO—, —SO$_2$—, —NR$^{10}$—, —C═C—, or —C≡C—. R$^{10}$ is an aliphatic hydrocarbon group having 1 to 4 carbon atoms, examples of which are the same as those of the above-mentioned aliphatic hydrocarbon group having 1 to 4 carbon atoms. When the interrupting group includes one or more carbon atoms, the total number of carbon atoms, including those in the interrupting group, is 1 to 4.

The aliphatic hydrocarbon groups, the aromatic hydrocarbon groups or the heterocyclic groups listed above may further be substituted. The aliphatic hydrocarbon groups, the aromatic hydrocarbon groups, and the aromatic heterocyclic groups may be substituted with groups such as a fluorine atom, a chlorine atom, a bromine atom, an iodine atom, a cyano group, a nitro group, a hydroxyl group, a thiol group, and an —NR$^7$R$^8$ group. R$^7$ and R$^8$ represent the same groups as those represented by R$^7$ and R$^8$, respectively, in formulae (A2-1) to (A2-15) shown below. When the aliphatic hydrocarbon group, the aromatic hydrocarbon group, or the heterocyclic group has a methylene moiety, its two hydrogen atoms may be replaced by one oxygen atom to form carbonyl.

Specific examples of a preferred group represented by Y include groups each represented by any of the partial structural formulae (Y-1) to (Y-12) shown below.

[Chemical Formula 2]

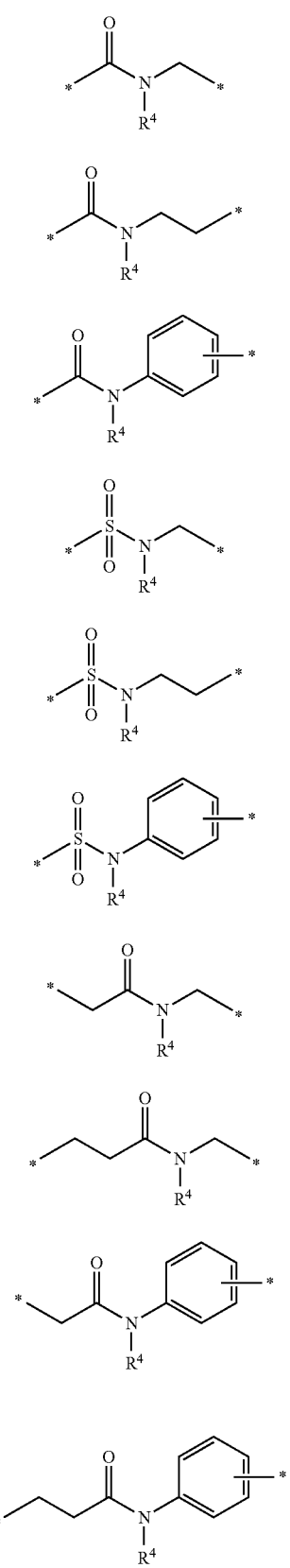

(Y-1)
(Y-2)
(Y-3)
(Y-4)
(Y-5)
(Y-6)
(Y-7)
(Y-8)
(Y-9)
(Y-10)

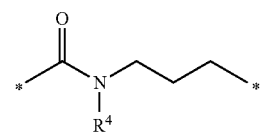

(Y-11)

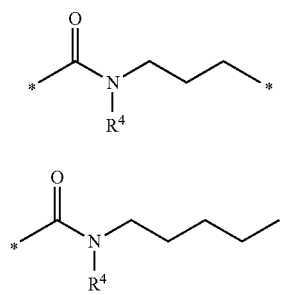

(Y-12)

Z is not particularly restricted as far as it is a π conjugated group, and it may have a substituent. In the invention, it is preferred that the π conjugated group represented by Z contains a nitrogen atom or that the substituent attached to Z is an amino group. In the invention, the term "π conjugated group" means to be formed from unsaturated bonds linked in series. The number of carbon atoms of the unsaturated bonds formed in series is preferably 4 to 60, more preferably 12 to 40, of the π conjugated groups represented by Z, from the viewpoint that the conversion efficiency of the working electrode (photoelectric conversion device) 10 is thereby increased successfully. When Z has a plurality of nitrogen atoms, the smallest number of the linked unsaturated bond carbon atoms is in the preferred range shown above.

Specific examples of a preferred π conjugated group represented by Z include groups each represented by any of the partial structural formulae (2-1) to (2-5) shown below.

[Chemical Formula 3]

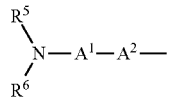

(2-1)

wherein $A^1$ is an optionally substituted aromatic hydrocarbon ring group or an optionally substituted aromatic heterocyclic group, $A^2$ represents a direct bond or a group comprising a chain of one to seven pieces of one or more groups selected from groups represented by the formulae (A2-1) to (A2-15) shown below, $R^5$ and $R^6$ each represent an optionally substituted hydrocarbon group, $R^5$ and $R^6$ may be linked together to form a ring, and $R^5$ and $R^6$ may be each independently linked with $A^1$ to form a ring,

[Chemical Formula 4]

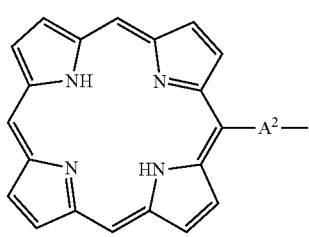

(2-2)

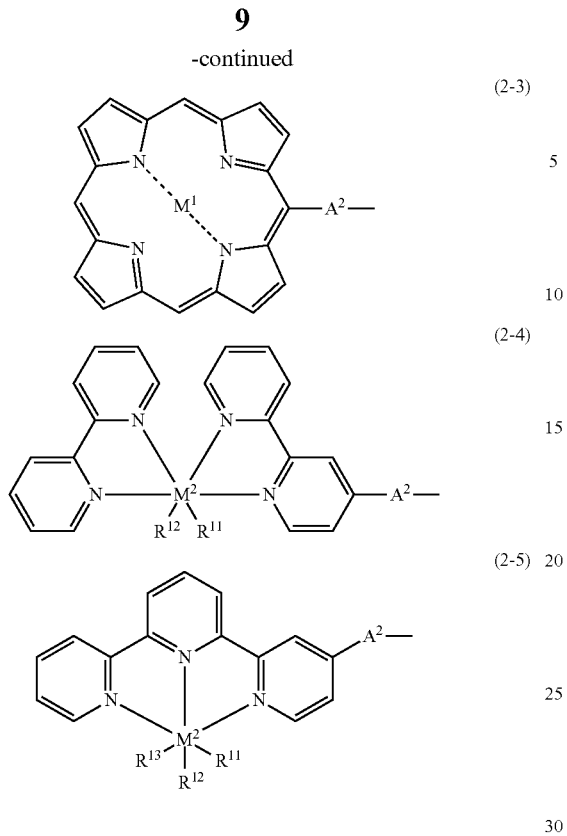

(2-3)

(2-4)

(2-5)

wherein $A^2$ represents a direct bond or a group comprising a chain of one to seven pieces of one or more groups selected from groups represented by the formulae (A2-1) to (A2-15) shown below, $R^{11}$, $R^{12}$, and $R^{13}$ each represent a known ligand that coordinates to $M^2$, $M^1$ and $M^2$ each represents a metal element, any hydrogen atoms in the formulae may be substituted with a fluorine atom, a chlorine atom, an iodine atom, a bromine atom, a cyano group, a nitro group, an —$OR^7$ group, an —$SR^7$ group, an optionally substituted aliphatic hydrocarbon group, or Y—$SiR^1R^2R^3$, wherein $R^1$, $R^2$, and $R^3$ represent groups the same as those in the above formula (1), and $R^7$ represents a hydrogen atom or an optionally substituted hydrocarbon group,

[Chemical Formula 5]

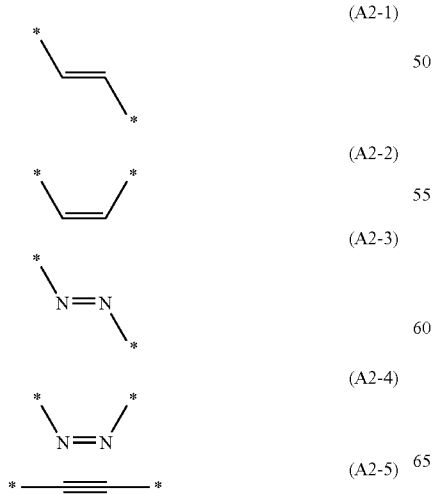

(A2-1)

(A2-2)

(A2-3)

(A2-4)

(A2-5)

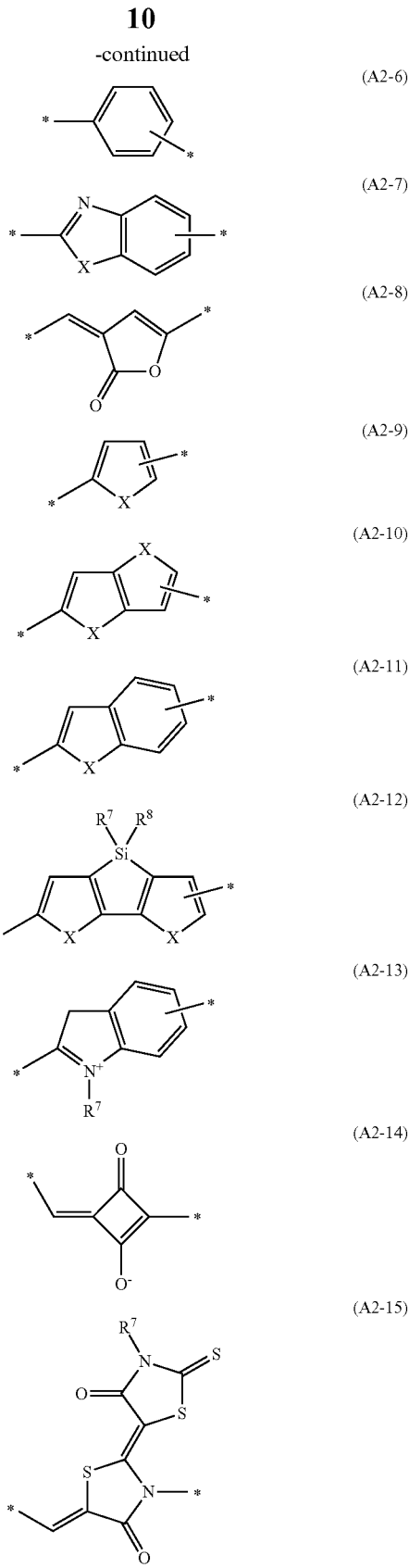

(A2-6)

(A2-7)

(A2-8)

(A2-9)

(A2-10)

(A2-11)

(A2-12)

(A2-13)

(A2-14)

(A2-15)

wherein X represents S, O, or NR, wherein R represents a hydrogen atom or an optionally substituted hydrocarbon group, and any hydrogen atom in the group may be substituted with a fluorine atom, a bromine atom, a chlorine atom, an iodine atom, a cyano group, a nitro group, an —OR$^7$ group, an —SR$^7$ group, an —NR$^7$R$^8$ group, or an optionally substituted aliphatic hydrocarbon group, wherein R$^7$ and R$^8$ each represent a hydrogen atom or an optionally substituted hydrocarbon group.

The group represented by A$^1$ in the above partial structural formula (2-1) is a divalent group which is an optionally substituted aromatic hydrocarbon ring group or an optionally substituted aromatic heterocyclic group.

Examples of the aromatic hydrocarbon ring group include an unsubstituted aromatic hydrocarbon ring group, an aliphatic hydrocarbon group-substituted aromatic hydrocarbon ring group, or the like. Examples of the aromatic heterocyclic group include an unsubstituted aromatic heterocyclic group, an aliphatic hydrocarbon group-substituted aromatic heterocyclic group, or the like.

Examples of the divalent unsubstituted aromatic hydrocarbon ring group include 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, anthracene-1,4-diyl, anthracene-1,5-diyl, anthracene-1,10-diyl, anthracene-9,10-diyl, perylene-3-10-diyl, perylene-3,10-diyl, pyrene-1,6-diyl, pyrene-2,7-diyl, or the like.

For example, the aliphatic hydrocarbon group-substituted divalent aromatic hydrocarbon ring group may have one to three aliphatic hydrocarbon groups of 1 to 20 carbon atoms as substituents on the divalent unsubstituted aromatic hydrocarbon ring.

Examples of the aliphatic hydrocarbon group of 1 to 20 carbon atoms include linear, branched, or cyclic alkyl groups such as methyl, ethyl, propyl, isopropyl, butyl, sec-butyl, tert-butyl, isobutyl, amyl, isoamyl, tert-amyl, hexyl, heptyl, isoheptyl, tert-heptyl, n-octyl, isooctyl, tert-octyl, nonyl, cyclopropyl, cyclobutyl, cyclopentyl, cyclohexyl, cycloheptyl, cyclooctyl, cyclononyl, and cyclodecyl. The aliphatic hydrocarbon group of 1 to 20 carbon atoms may be interrupted by —O—, —COO—, —COO—, —CO—, —S—, —SO—, —SO2-, —NR$^9$—, —C=C—, or —C≡C—. R$^9$ is an aliphatic hydrocarbon group of 1 to 20 carbon atoms, which may be exemplified by the same groups as the above aliphatic hydrocarbon group of 1 to 20 carbon atoms. When the interrupting group has one or more carbon atoms, the total number of carbon atoms, including those in the interrupting group, is from 1 to 20.

Examples of the divalent unsubstituted aromatic heterocyclic group include furan-2,5-diyl, furan-3,5-diyl, thiophene-2,5-diyl, thiophene-3,5-diyl, 2H-chromene-3,7-diyl, benzothiophene-2,6-diyl, benzothiophene-2,5-diyl, or the like.

Examples of the aliphatic hydrocarbon group-substituted divalent aromatic heterocyclic group include 1-alkyl-pyrrole-2,5-diyl, 1-alkyl-pyrrole-3,5-diyl, or the like and a group having one to three aliphatic hydrocarbon groups of 1 to 20 carbon atoms as substituents on the divalent unsubstituted aromatic heterocyclic group. The aliphatic hydrocarbon group of 1 to 20 carbon atoms may be exemplified by the same groups as the above aliphatic hydrocarbon group of 1 to 20 carbon atoms.

The aromatic hydrocarbon ring groups or the aromatic heterocyclic groups listed above may further have a substituent(s). The aromatic hydrocarbon ring groups and the aromatic heterocyclic groups may be substituted with substituents such as a fluorine atom, a chlorine atom, a bromine atom, an iodine atom, a cyano group, a nitro group, a hydroxyl group, a thiol group, or an —NR$^7$R$^8$ group. R$^7$ and R$^8$ represent the same groups as those represented by R$^7$ and R$^8$, respectively, in the above formulae (A2-1) to (A2-15). When the aromatic hydrocarbon ring group or the aromatic heterocyclic group has a methylene moiety, its two hydrogen atoms may be replaced by one oxygen atom to form carbonyl.

The group represented by A$^2$ in the above formulae (2-1) to (2-5) is a direct bond or a group comprising a chain of one to seven, preferably one to four, more preferably two to four, pieces of one or more groups selected from the groups represented by the above formulae (A2-1) to (A2-15). Pieces of each group represented by any of the above formulae (A2-1) to (A2-15) may be linked in any direction. The mark * in the group represented by each of the above formulae (A2-1) to (A2-15) indicates the position to which the adjacent group is to be linked (the same applies hereinafter).

In the above formulae (A2-1) to (A2-15), X represents S, O, or NR, wherein R represents a hydrogen atom or an optionally substituted hydrocarbon group. Examples of the optionally substituted hydrocarbon group represented by R are the same as those of the optionally substituted hydrocarbon group represented by R$^1$, R$^2$, and R$^3$ described below.

Any hydrogen atom in the groups represented by the above formulae (A2-1) to (A2-15) may be substituted with a fluorine atom, a chlorine atom, a bromine atom, an iodine atom, a cyano group, a nitro group, an —OR$^7$ group, an —SR$^7$ group, an —NR$^7$R$^8$ group, or an optionally substituted aliphatic hydrocarbon group, wherein R$^7$ and R$^8$ each represent a hydrogen atom or an optionally substituted hydrocarbon group. Groups as substituents on the A$^2$ groups may be linked together to form a ring.

For example, the optionally substituted aliphatic hydrocarbon group may be the above aliphatic hydrocarbon group of 1 to 20 carbon atoms, and the groups may be substituted with the substituents listed above for the aromatic hydrocarbon ring group and the aromatic heterocyclic group.

Examples of the optionally substituted hydrocarbon groups represented by R$^7$ and R$^8$ are the same as those of the optionally substituted hydrocarbon groups represented by R$^1$, R$^2$, and R$^3$ described below.

Specific examples of the structure of the A$^1$-A$^2$ moiety in the above partial structural formula (2-1) include the structures represented by any of A(1) to A(35) shown below. In each of the examples of the A moiety shown below, the ring structure at the left end corresponds to A$^1$, and the other part corresponds to A$^2$.

Although the examples shown below have no substituents, the A$^1$ moiety may have a substituent(s) and any hydrogen atom in the A$^2$ moiety may be substituted with a substituent as described above. In each of A(16) to A(23) shown below, each bond drawn across two or more rings means that the bond may be attached to any of the carbon atoms in these rings (the same applies hereinafter).

[Chemcial Formula 6]

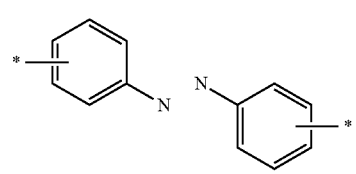

A(1)

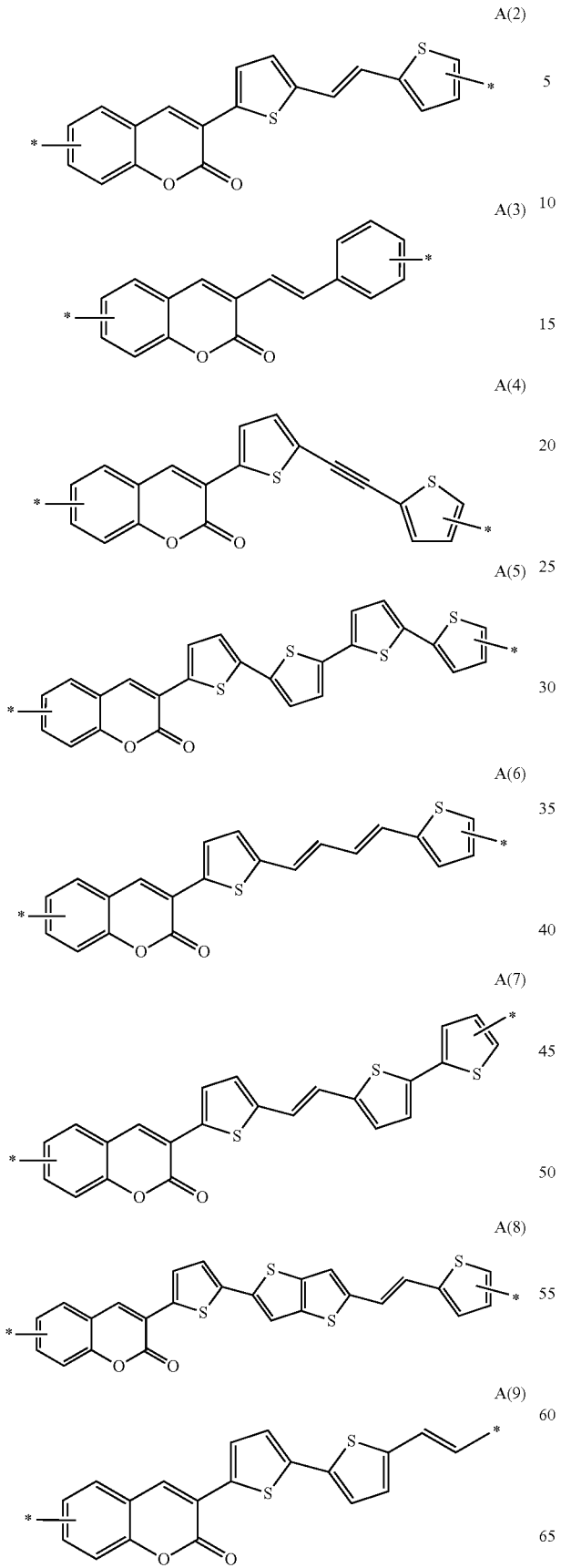
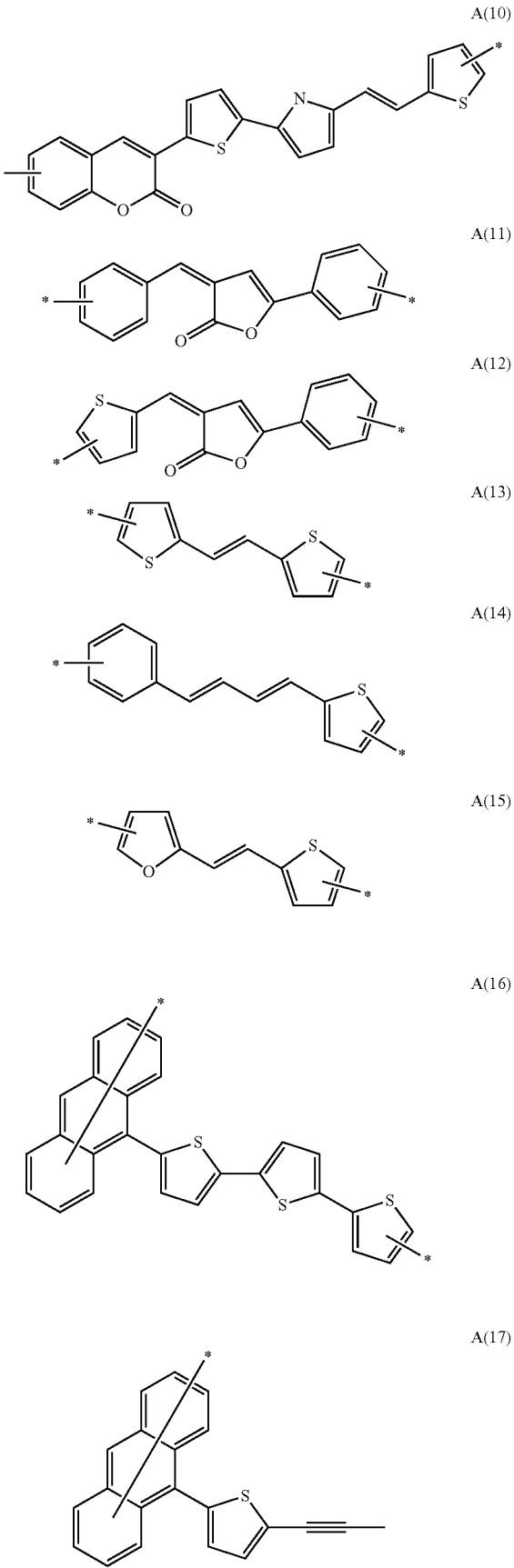

A(18)
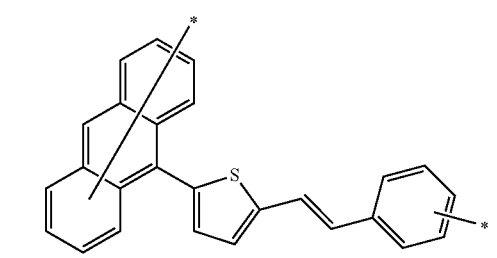
A(19)
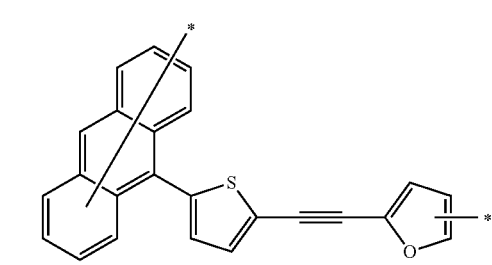
A(20)
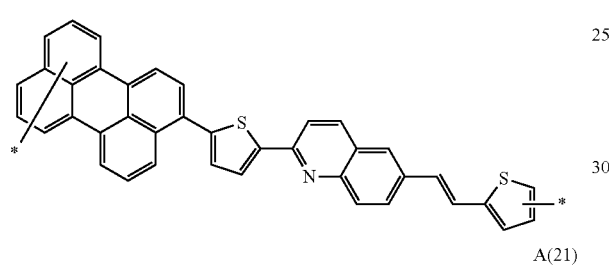
A(21)
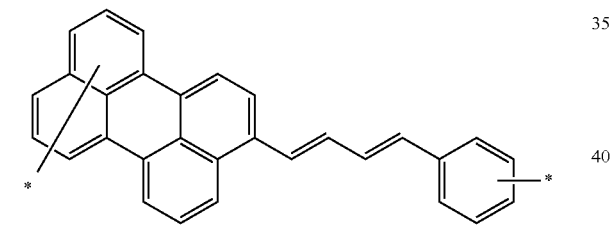
A(22)
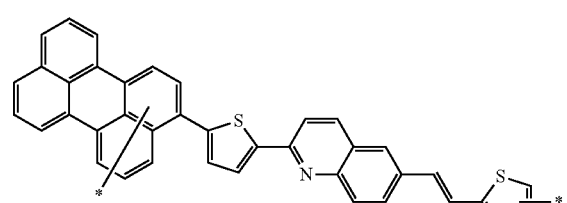
A(23)
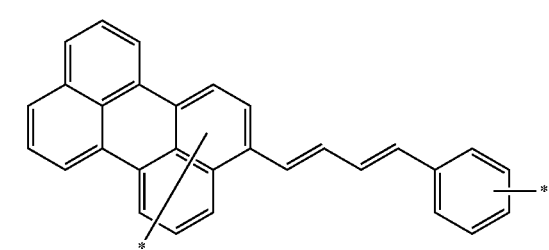
A(24)
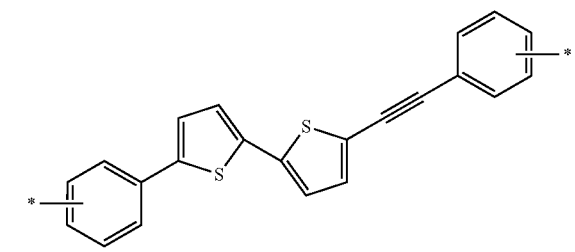
A(25)
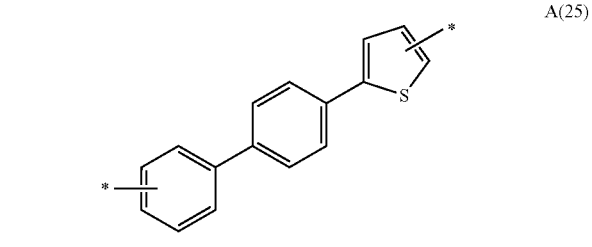
A(26)
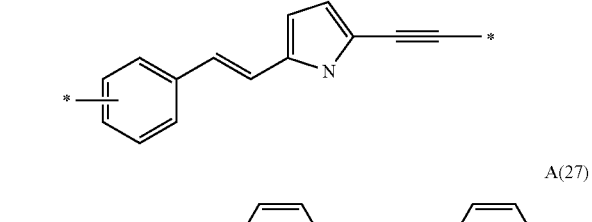
A(27)
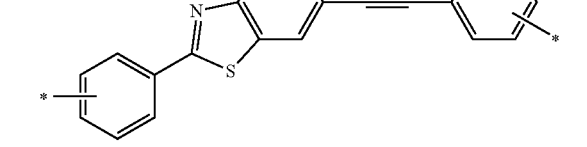
A(28)
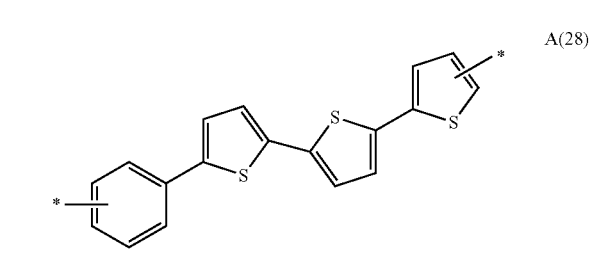
A(29)
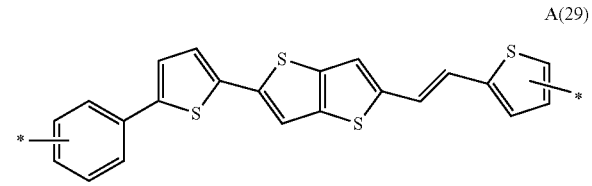
A(30)

-continued

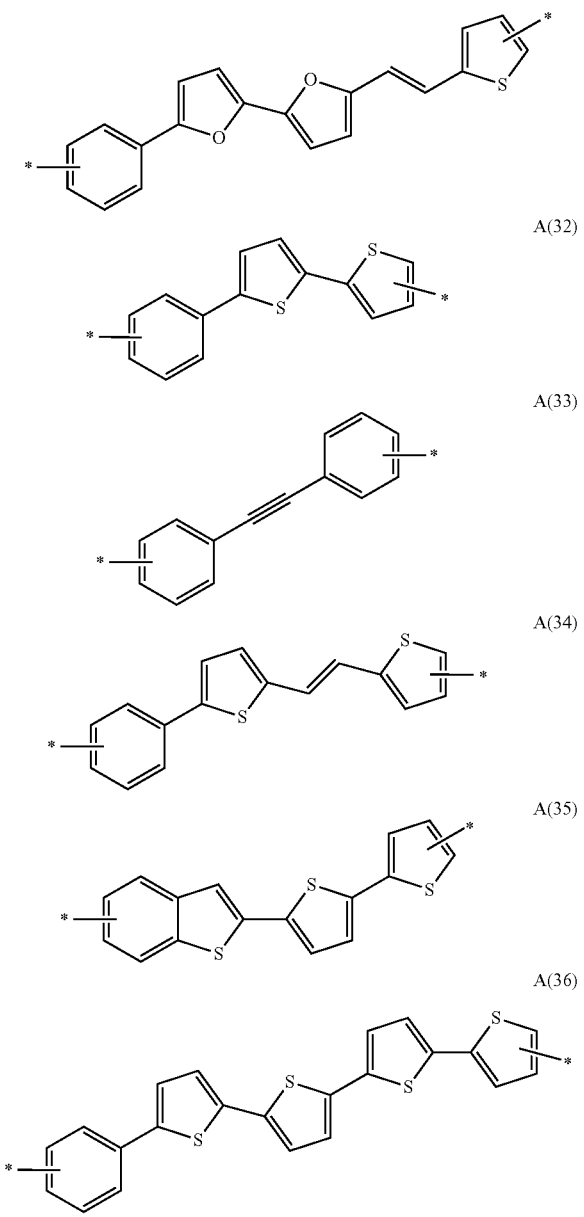

In formula (1), the hydrocarbon group of the optionally substituted hydrocarbon group represented by $R^1$, $R^2$, and $R^3$ may be an aromatic hydrocarbon group, an aliphatic hydrocarbon group-substituted aromatic hydrocarbon group, an aliphatic hydrocarbon group, or the like.

The aromatic hydrocarbon group may be phenyl, naphthyl, cyclohexylphenyl, biphenyl, terphenyl, fluorenyl, thiophenylphenyl, furanylphenyl, 2'-phenyl-propylphenyl, benzyl, naphthylmethyl, or the like. Examples of the aliphatic hydrocarbon group include the aliphatic hydrocarbon groups having 1 to 20 carbon atoms described for $A^1$. The aliphatic hydrocarbon group-substituted aromatic hydrocarbon group may be phenyl, naphthyl, benzyl or the like substituted with the aliphatic hydrocarbon group.

These hydrocarbon groups may be substituted with a substituent such as a fluorine atom, a chlorine atom, a bromine atom, an iodine atom, a cyano group, a nitro group, a hydroxyl group, a thiol group, an $—NR^7R^8$ group, or the like, wherein $R^7$ and $R^8$ represent the same groups as $R^7$ and $R^8$ described above for $A^2$.

In formula (1), the optionally substituted hydrocarbonoxy group represented by $R'$, $R^2$, and $R^3$ may has an optionally substituted hydrocarbon moiety, which can be exemplified by the same groups as the optionally substituted hydrocarbon group represented by $R^1$ described above, and an —O— moiety, which is interposed between the hydrocarbon moiety and the Si atom.

At least one of $R^1$, $R^2$, and $R^3$ represents an optionally substituted hydrocarbonoxy group. In terms of the high ability to adsorb to the support described below, it is preferable that at least one of $R^1$, $R^2$, and $R^3$ is an aliphatic hydrocarbonoxy group, or all of $R^1$, $R^2$, and $R^3$ are optionally substituted hydrocarbonoxy groups. It is more preferable that two or three of $R^1$, $R^2$, and $R^3$ are each a linear or branched aliphatic hydrocarbonoxy group (especially of 1 to 5 carbon atoms), and none or one of them is a linear or branched aliphatic hydrocarbon group (especially of 1 to 5 carbon atoms). It is most preferable that all of $R^1$, $R^2$, and $R^3$ are each a linear or branched aliphatic hydrocarbonoxy group (especially of 1 to 5 carbon atoms).

In the above partial structural formula (2-1), the optionally substituted hydrocarbon group represented by $R^5$ and $R^6$ may be the group described above as the optionally substituted hydrocarbon group represented by $R^1$. $R^5$ and $R^6$ may be linked together to form a ring, and $R^5$ and $R^6$ may each independently be linked with $A^1$ to form a ring.

In the above formula (2-3), specific examples of the metal element of $M^1$ include Cu, Mg, Ca, Sr, Ba, Sc, Y, La, Ce, Pr, Nd, Sm, Eu, Gd, Tb, Dy, Ho, Sn, Yb, Ti, Zr, Hf, V, Nb, Ta, Th, U, Mn, Cr, Fe, Co, Zn, Mo, Ni, Rh, or the like; of these, Cu, Ti, Ni, Fe, or Zn is preferred, and Cu or Zn is more preferred.

In the above formulae (2-4) and (2-5), the metal element of $M^2$ represents a metal capable of forming tetra-coordination or hexa-coordination, and it is preferably Ru, Fe, Os, Cu, W, Cr, Mo, Ni, Pd, Pt, Co, Ir, Rh, Re, Mn, or Zn, more preferably Ru, Fe, Os, or Cu, and particularly preferably Ru.

In the above formulae (2-4) and (2-5), the known ligand that coordinates to $M^2$ represented by $R^{11}$, $R^{12}$, and $R^{13}$ is a unidentate, bidentate, or tridentate ligand, and the ligand may be either a neutral ligand or an anionic ligand. While specific ligands are not particularly restricted, a halogen atom, —NCS, oxalic acid, or the like are preferred, and a halogen atom or —NCS is more preferred.

Of the compounds represented by the above formula (2-1), the compounds in which the partial structure (3) shown below is any one of the partial structures (3-1) to (3-10) shown below are preferred because they exhibit particularly good properties for photoelectric conversion applications. The compound having the partial structure (3-1), (3-2), or (3-7) shown below is particularly preferred because it is easy to produce and has high efficiency of electron injection into a metal oxide semiconductor.

In the partial structures (3) and (3-1) to (3-8) shown below, a mark of the bond of $A^1$ to $A^2$ is omitted. In the partial structures (3-1) to (3-8) shown below, the bond of $A^1$ to $A^2$ may be attached to any carbon atom of the aromatic hydrocarbon ring and the aromatic heterocyclic ring.

[Chemical Formula 7]

(3)

wherein A¹, R⁵, and R⁶ are the same as those of the above partial structural formula (2-1),

[Chemical Formula 8]

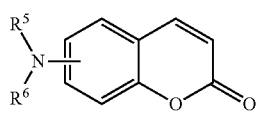
(3-1)

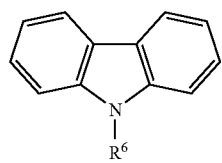
(3-2)

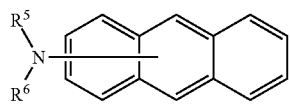
(3-3)

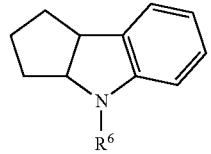
(3-4)

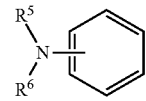
(3-5)

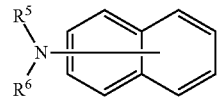
(3-6)

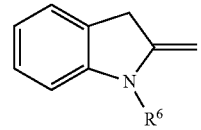
(3-7)

(3-8)

wherein $R^5$ and $R^6$ are the same as those of the above partial structural formula (2-1), any hydrogen atoms in the formulae may be substituted with a fluorine atom, a chlorine atom, an iodine atom, a bromine atom, a cyano group, a nitro group, an —$OR^7$ group, an —$SR^7$ group, an optionally substituted aliphatic hydrocarbon group, or Y—$SiR^1R^2R^3$, wherein $R^1$, $R^2$, and $R^3$ represent groups the same as those in the above formula (1), and $R^7$ represents a hydrogen atom or an optionally substituted hydrocarbon group.

Of the compounds represented by the above formula (1), compounds in which the group represented by Y is an optionally substituted hydrocarbon group having 1 to 20 carbon atoms and having —CO—$NR^4$— or —$SO_2$—$NR^4$— in the group are preferred because they are particularly easy to produce.

Specific examples of the compound represented by the above formula (1) include, but are not limited to, compounds Nos. 1 to 135 shown below. In the formula, Me represents a methyl group, Et represents an ethyl group, Pr represents a propyl group, Bu represents a butyl group, Hex represents a hexyl group, Oct represents an octyl group, Non represents a nonyl group, Dec represents a decyl group, and TBA represents a tetrabutylammonium group.

[Chemical Formula 9]

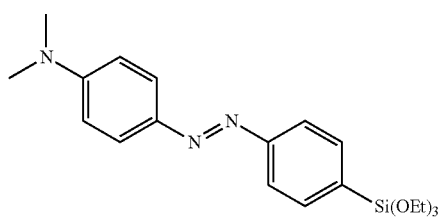
NO.1

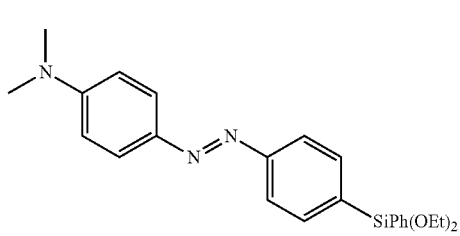
No.2

-continued
No. 3
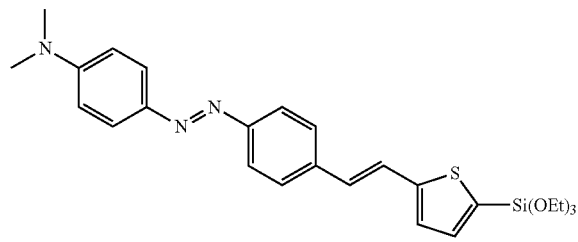
NO. 4
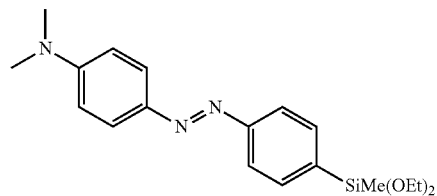
No. 5
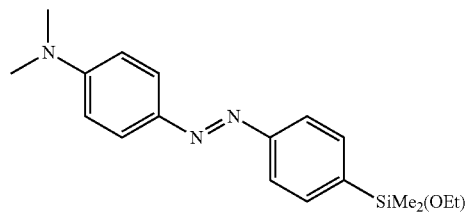
NO. 6
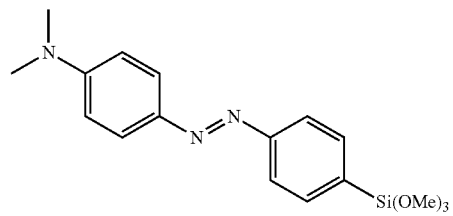
No. 7
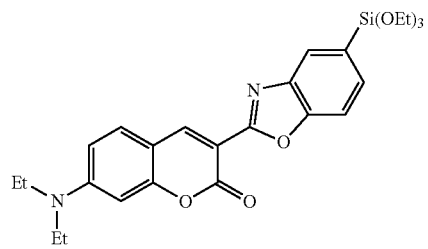
No. 8
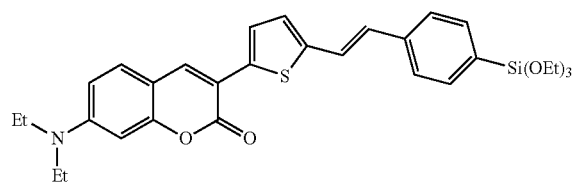
No. 9
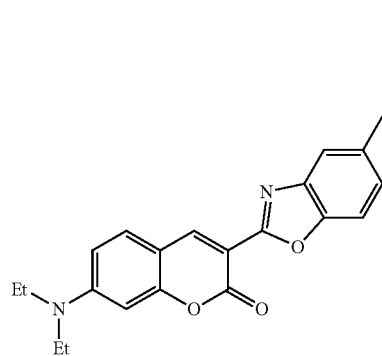
No. 10
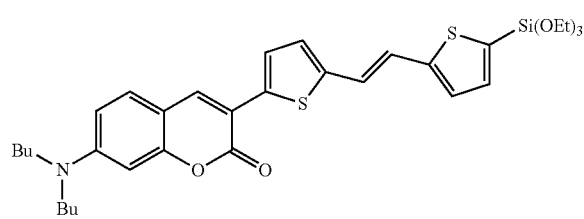
No. 11
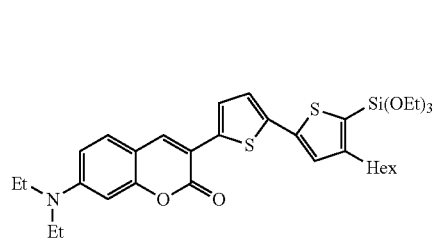
No. 12
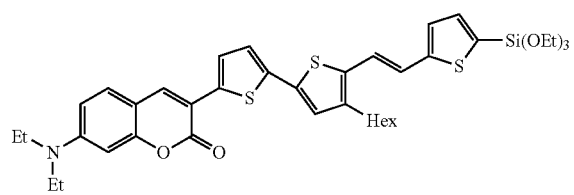
No. 13
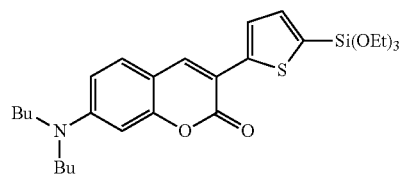
No. 14
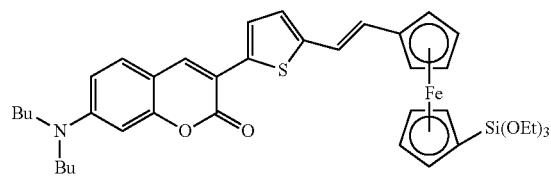

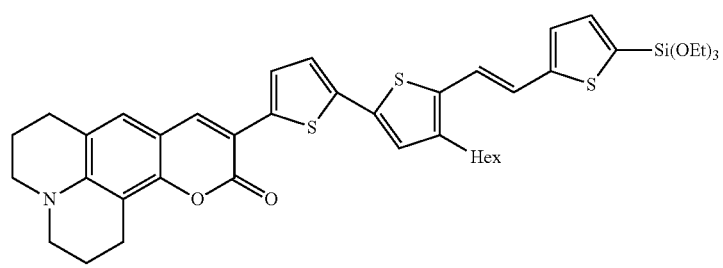
No. 15
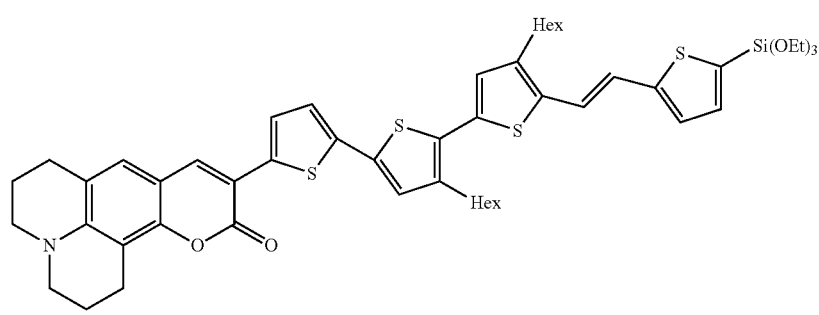
No. 16
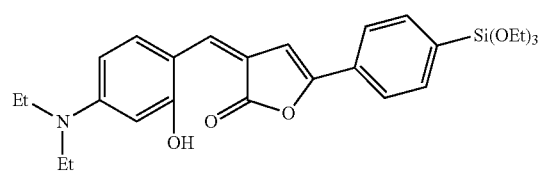
No. 17
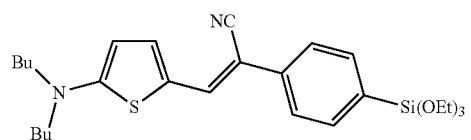
No. 18
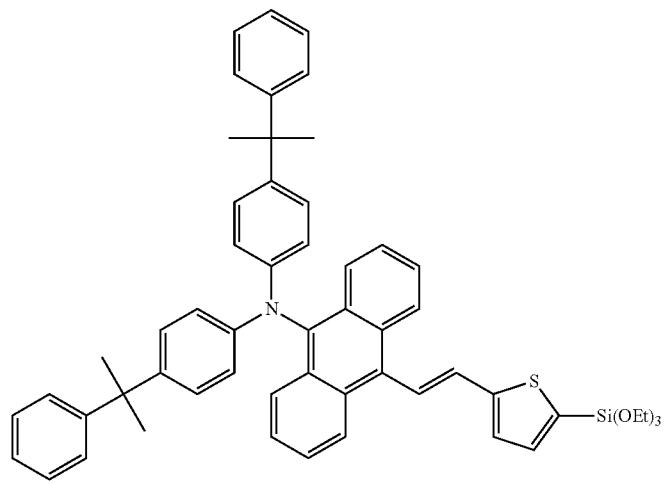
No. 19

[Chemical Formula 10]
No. 20
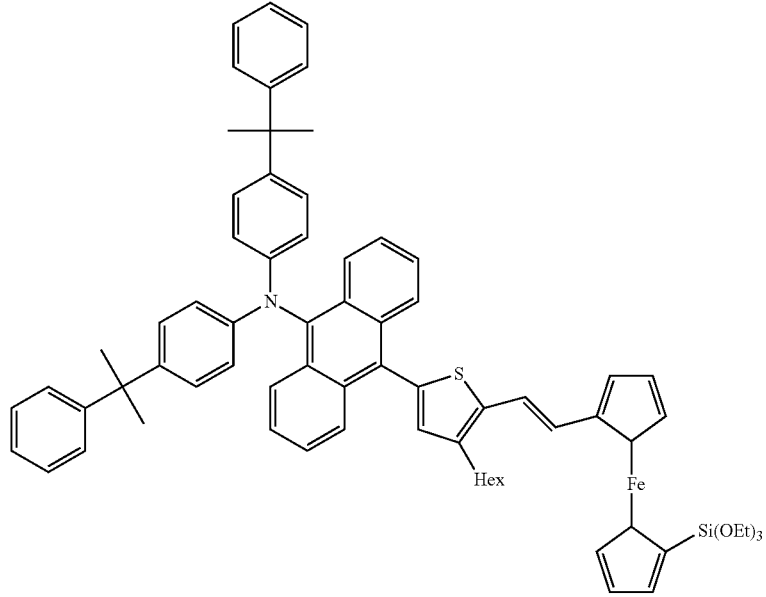
No. 21
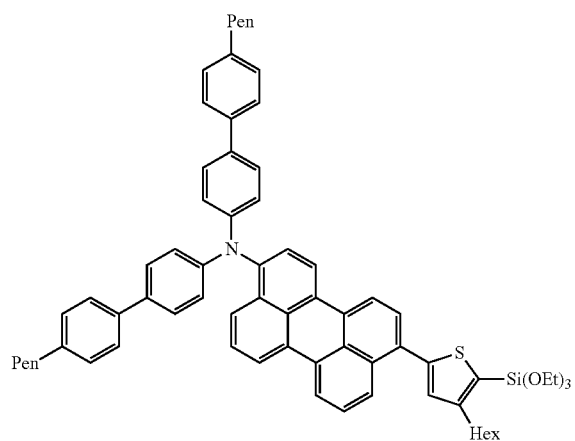
No. 22
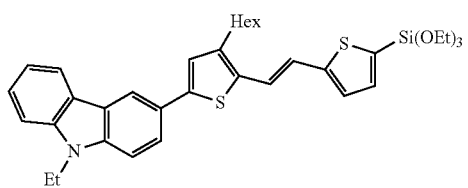
No. 23
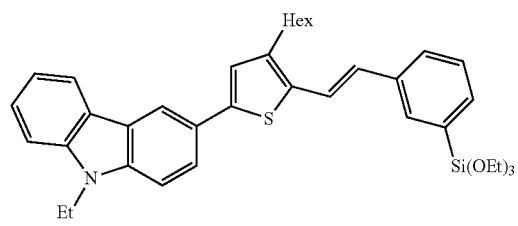
No. 24
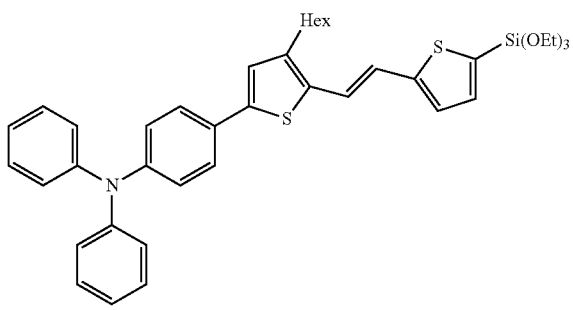

-continued
No. 25
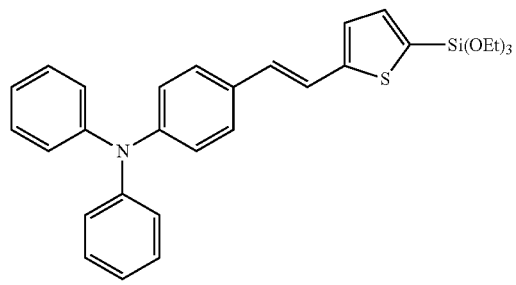
No. 26
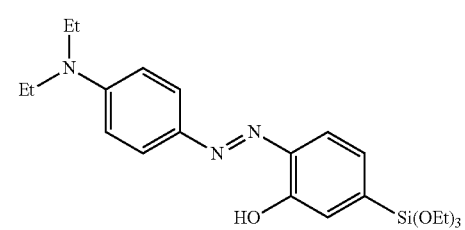
No. 27
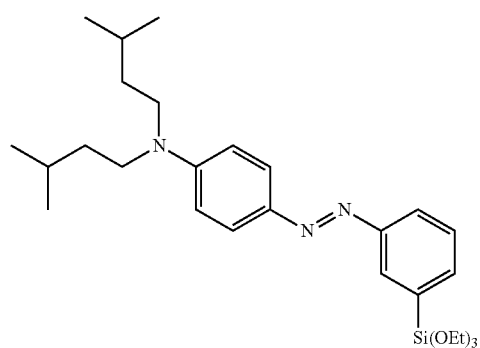
No. 28
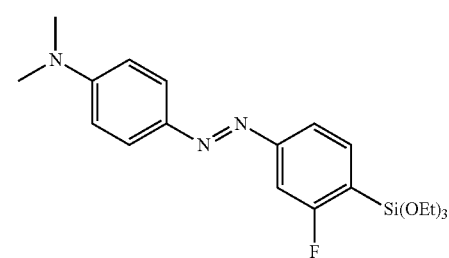
No. 29
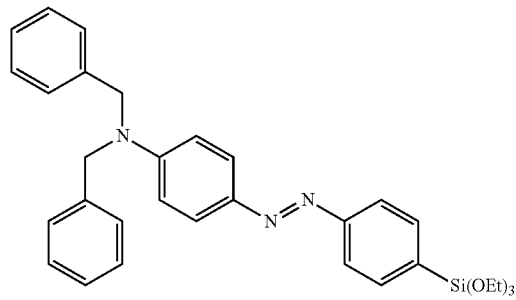
No. 30
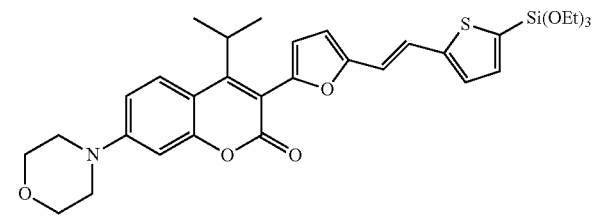
No. 31
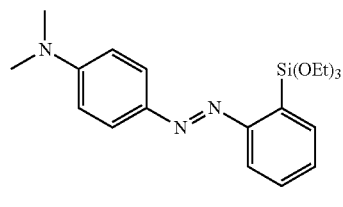
No. 32
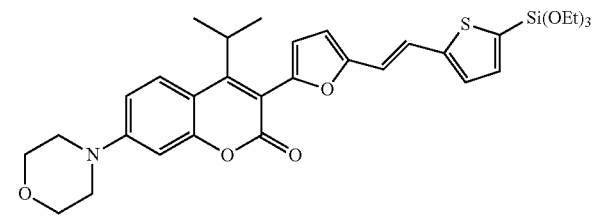
No. 33
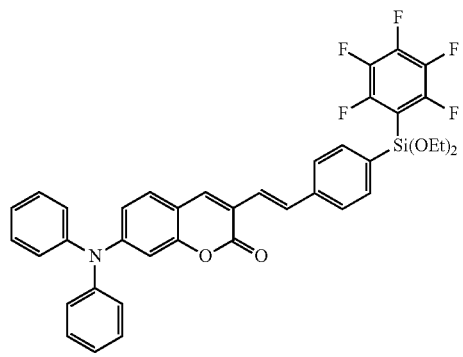
No. 34
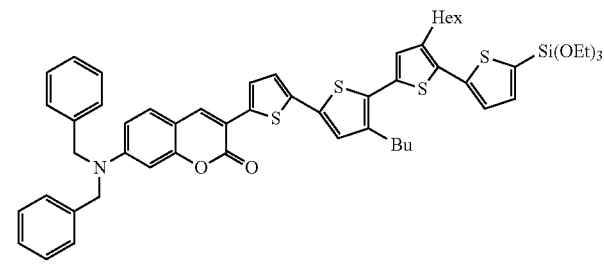

No. 35
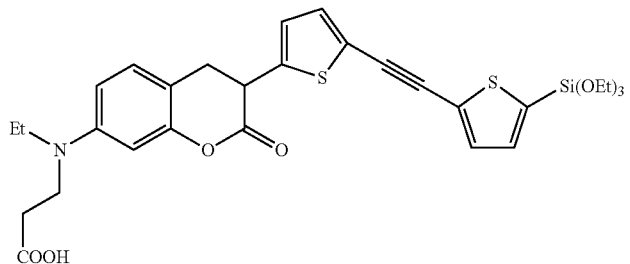
No. 36
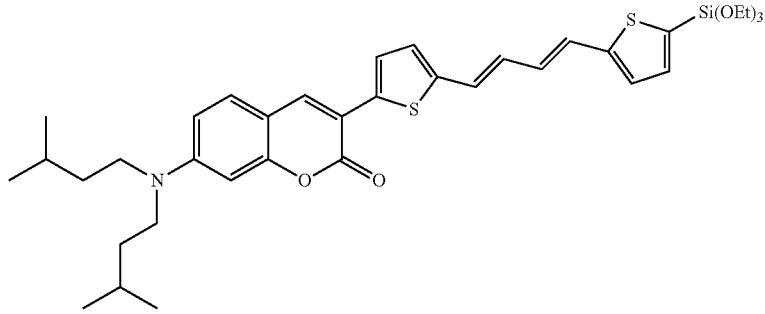
No. 37
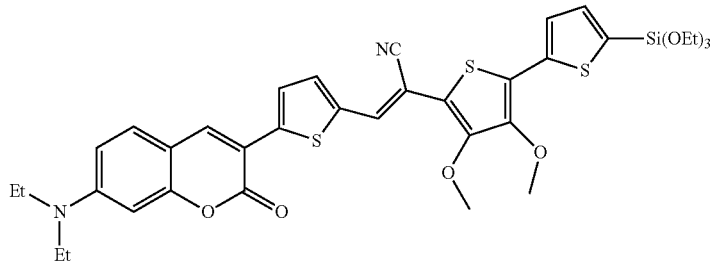
[Chemical Formula 11]
No. 38
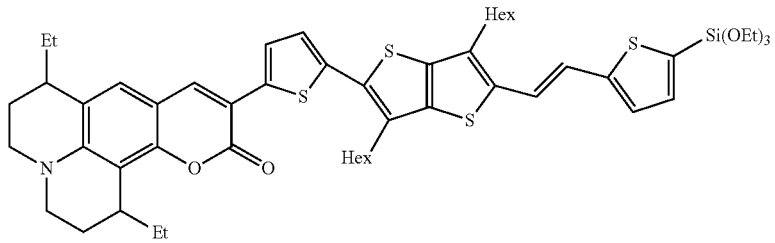
No. 39
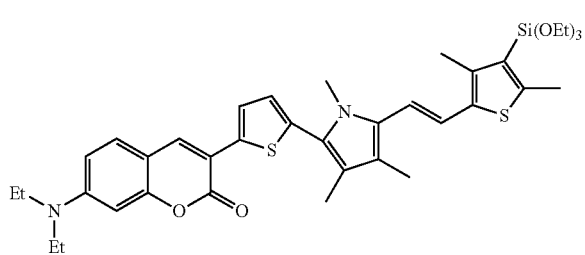
No. 40
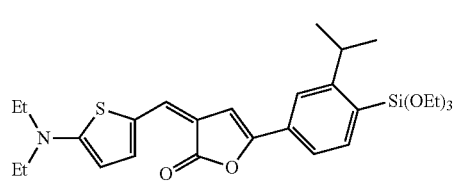
No. 41
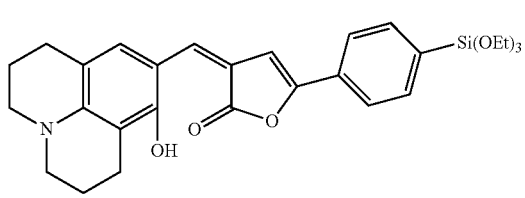
No. 42
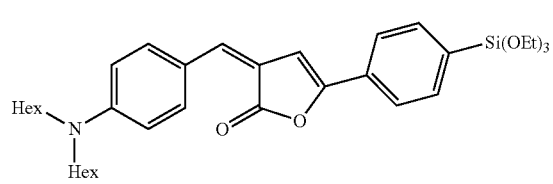

-continued
No. 43 No. 44
No. 45 No. 46
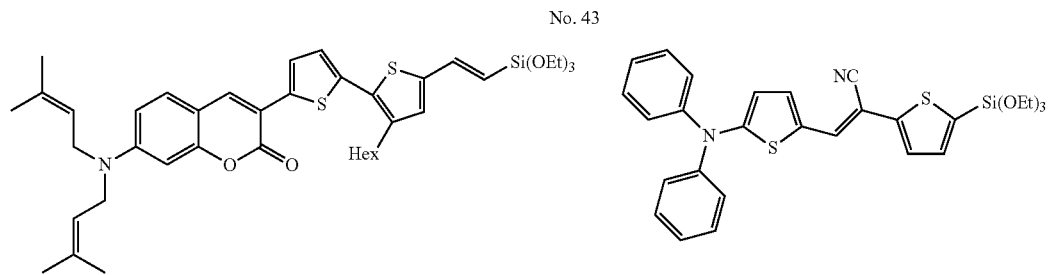
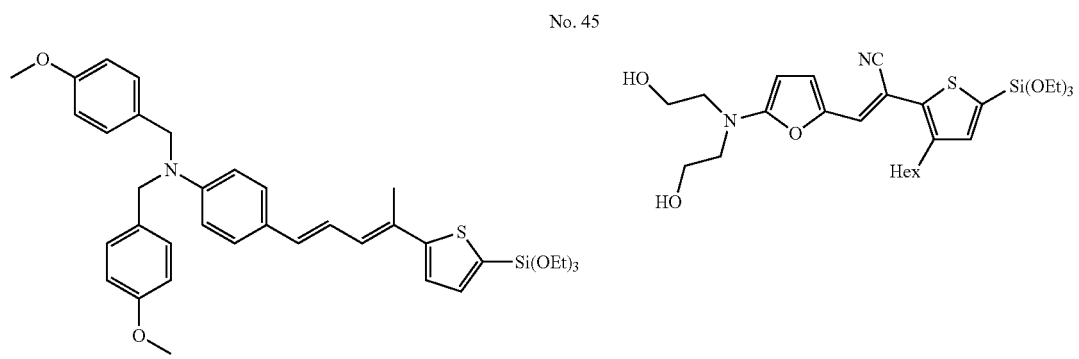
No. 47 No. 48
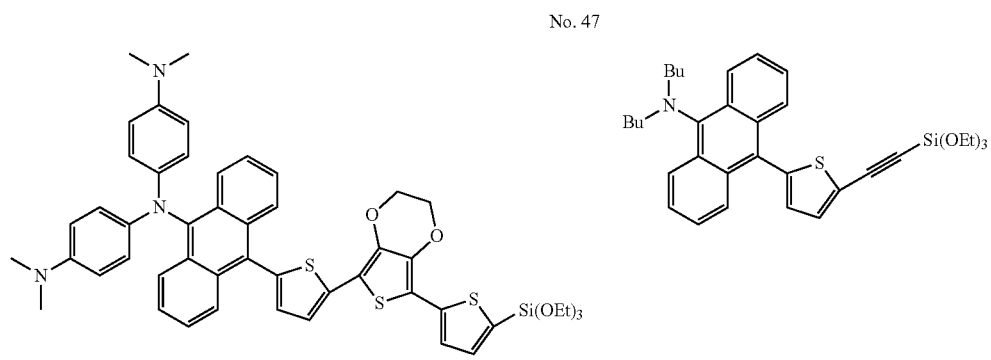
No. 49 No. 50
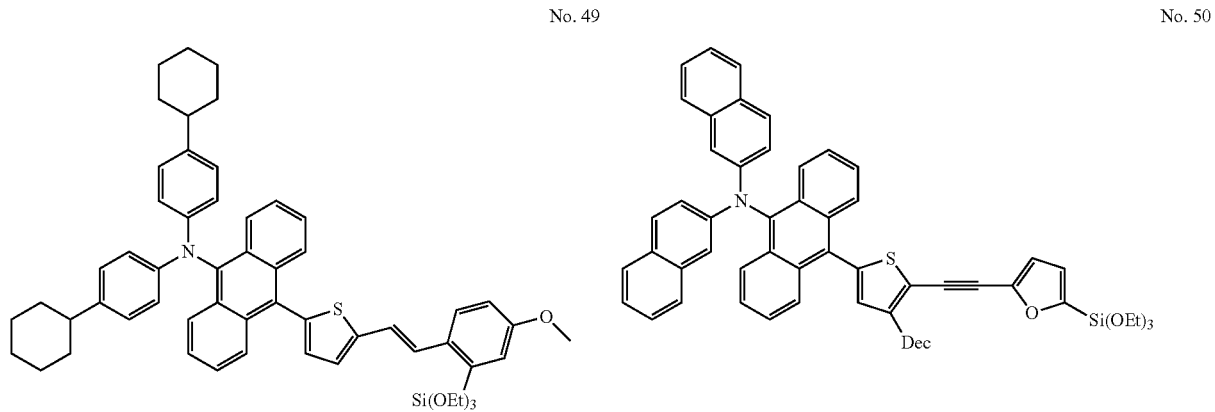

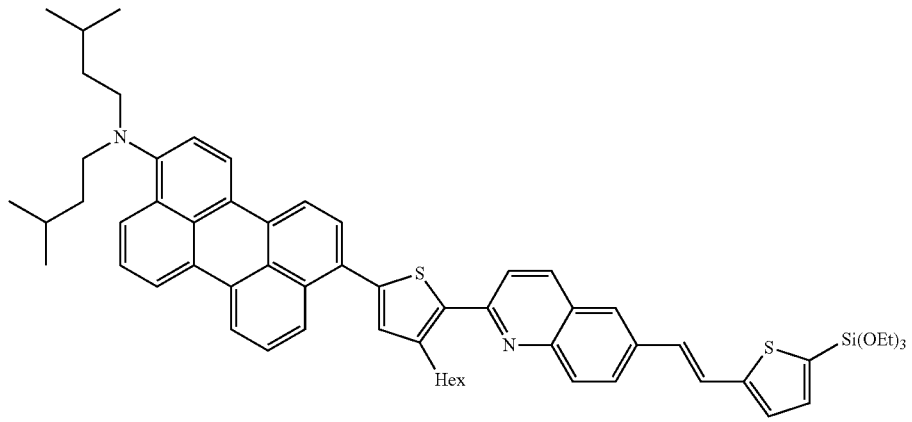
No. 51
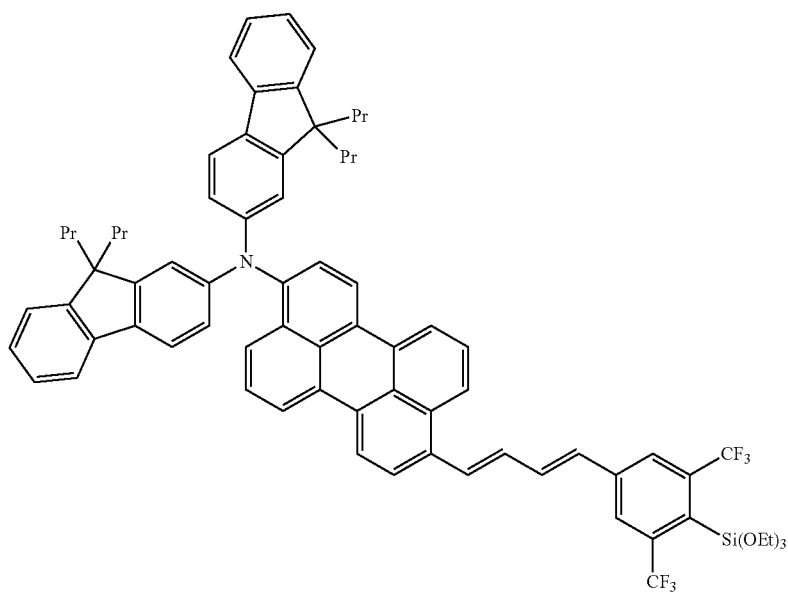
No. 52
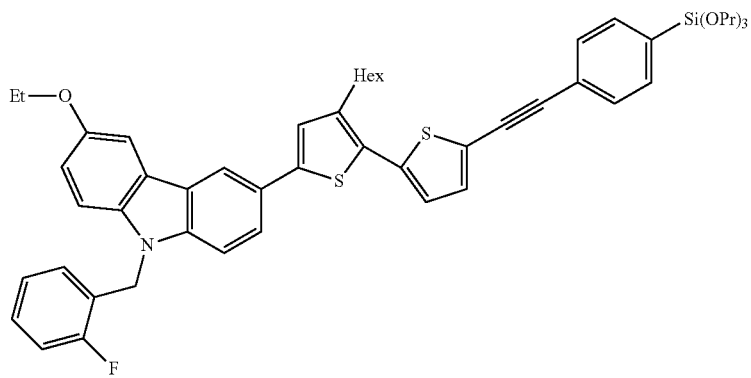
No. 53

[Chemical Formula 12]
No. 54
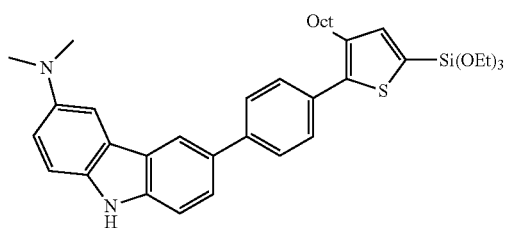
No. 55
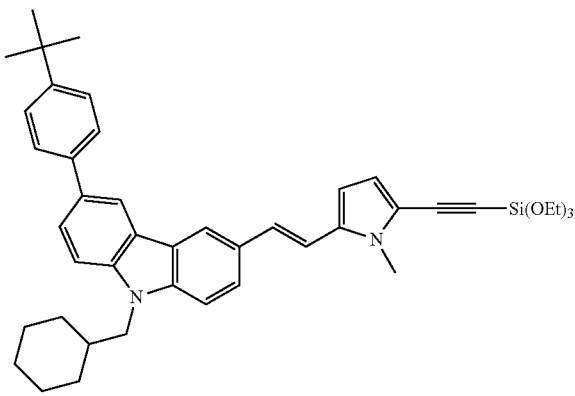
No. 56
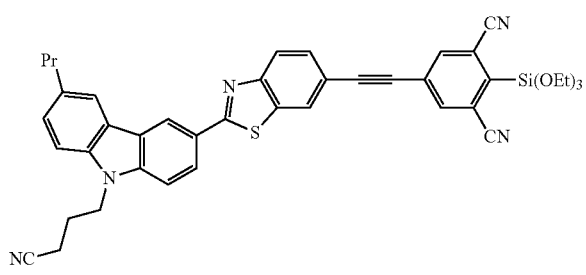
No. 57
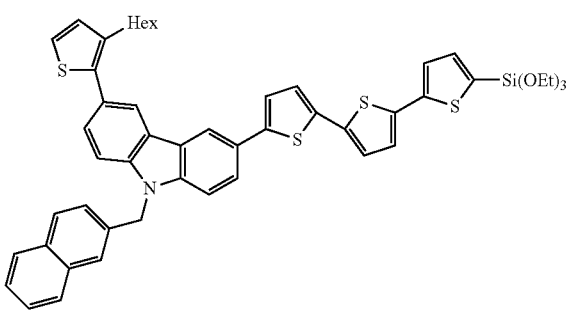
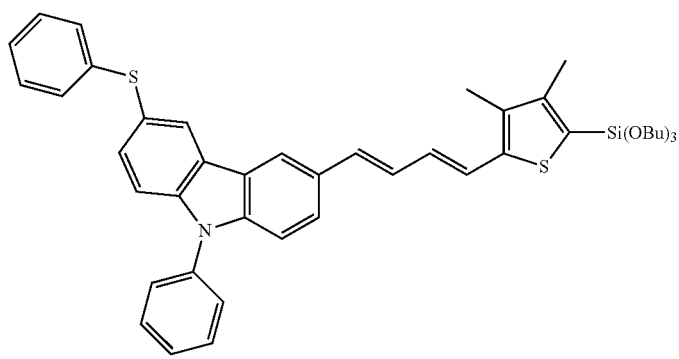
No. 58
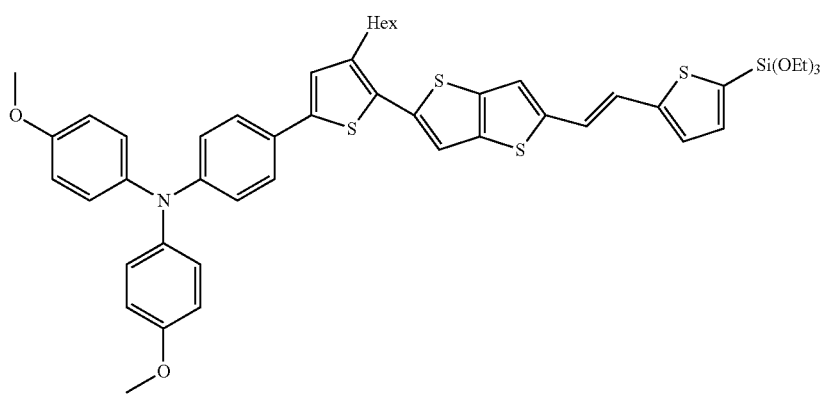
No. 59

-continued
No. 60
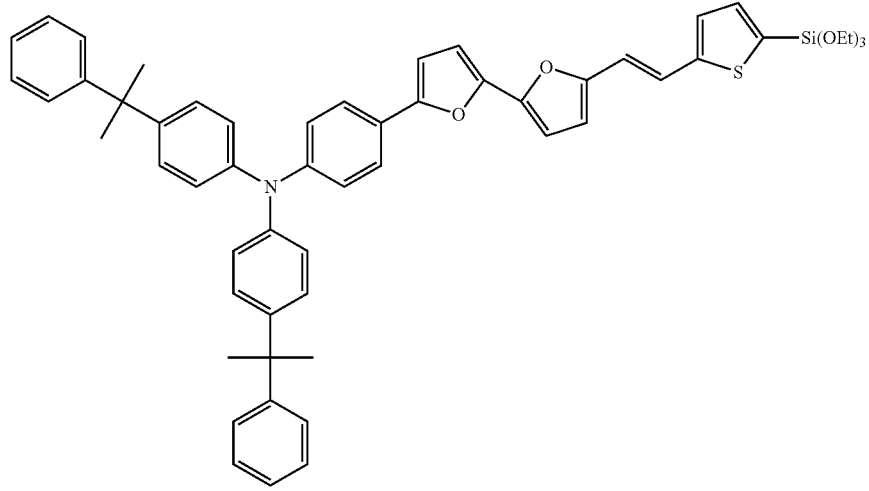
No. 61
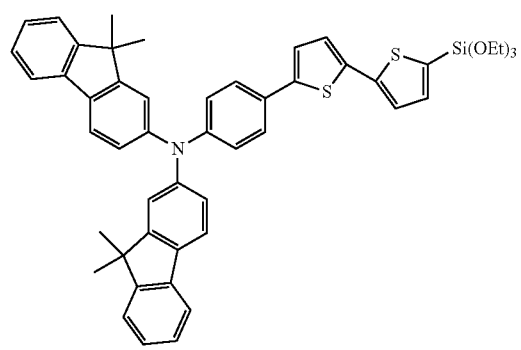
No. 62
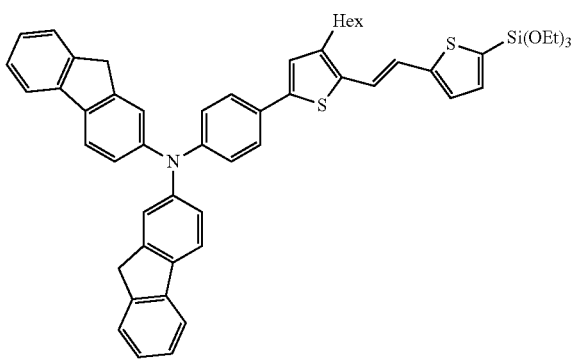
No. 63
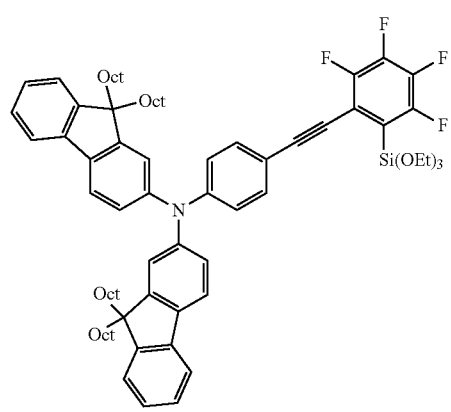
No. 64
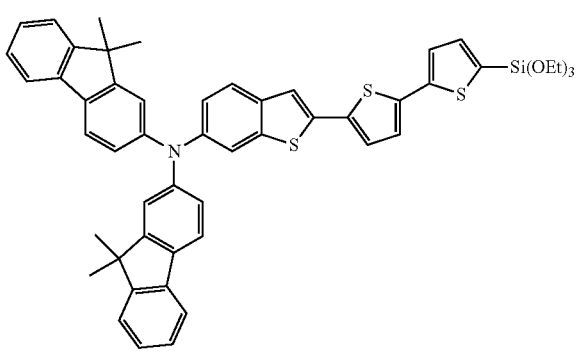
No. 65
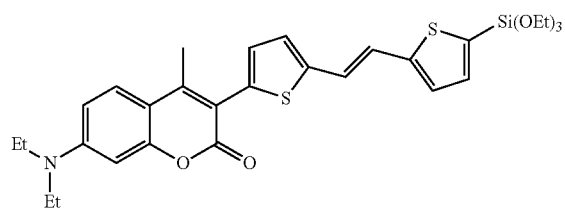
No. 66
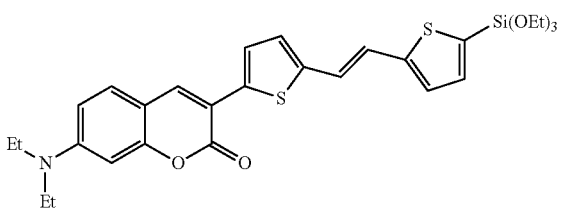

[Chemical Formula 13]
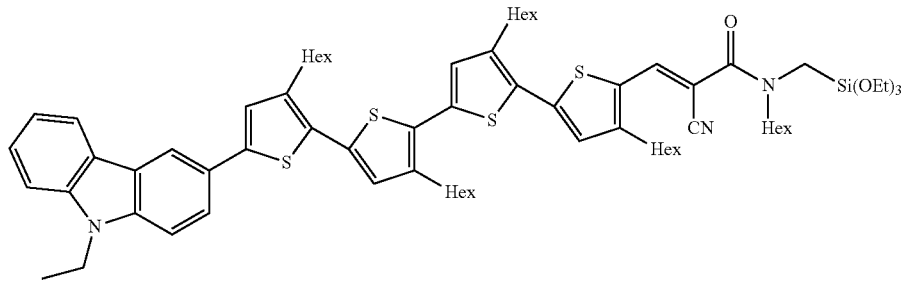 No. 67
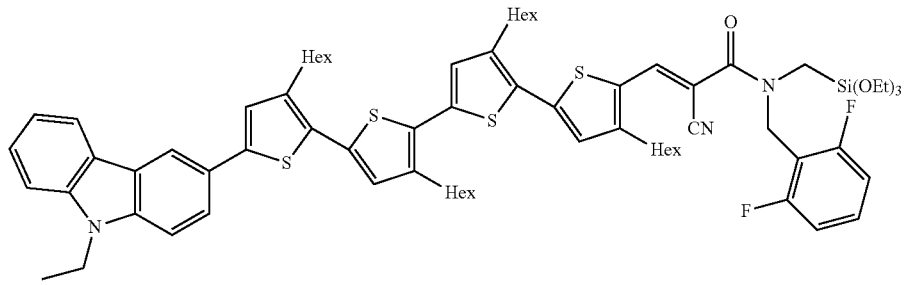 No. 68
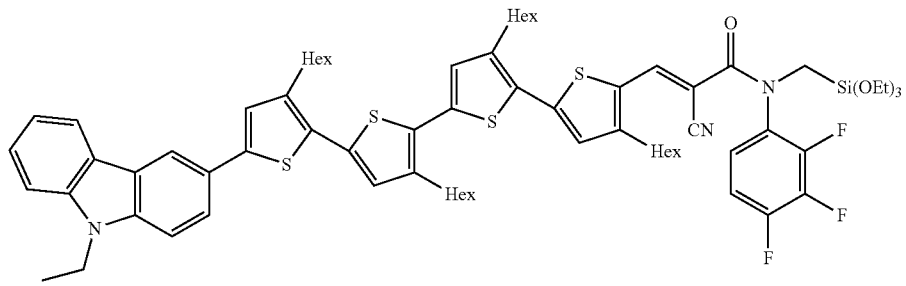 No. 69
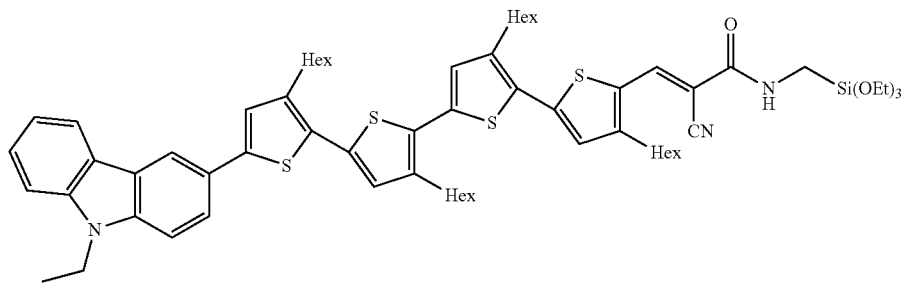 No. 70
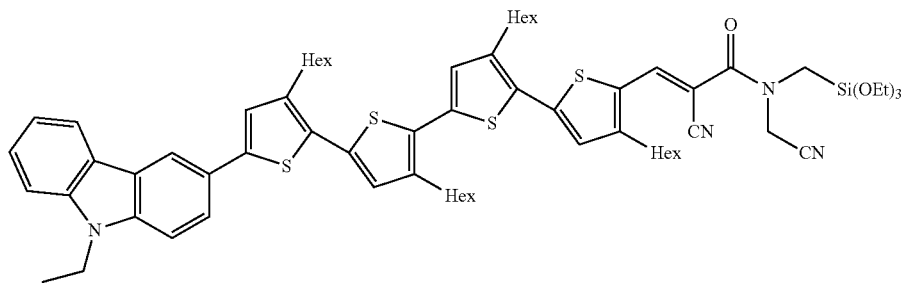 No. 71

-continued
No. 72
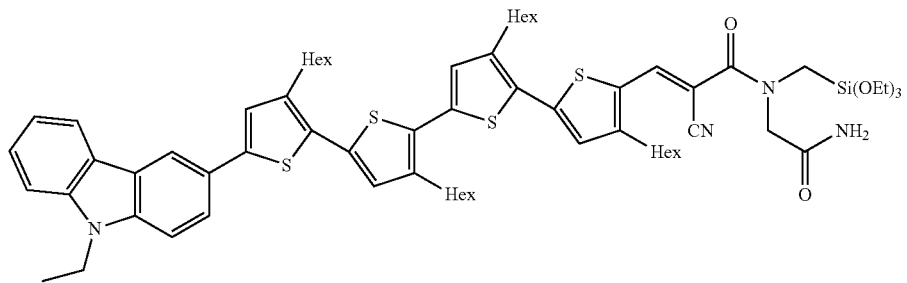
No. 73
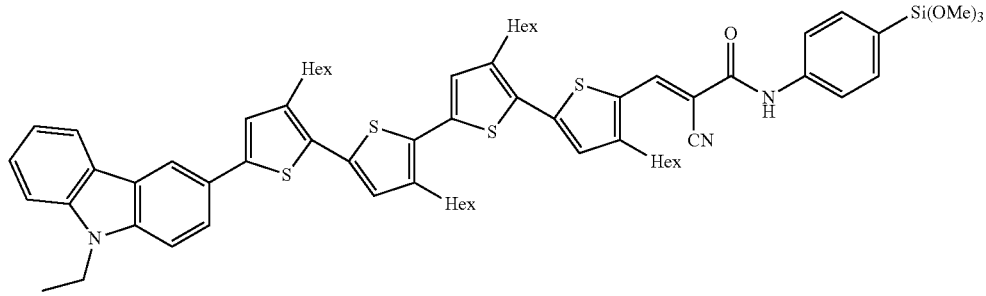
No. 74
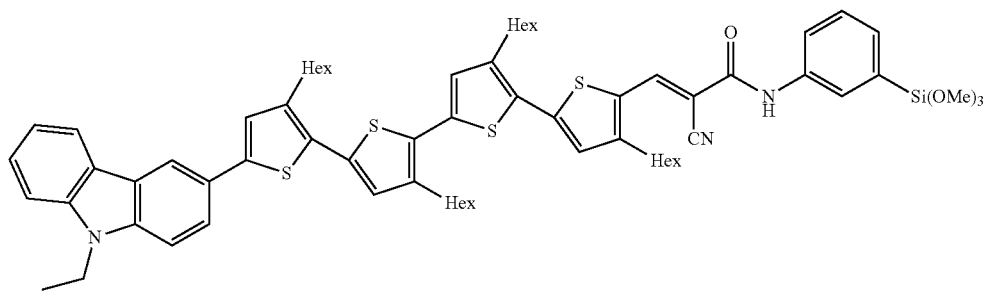
No. 75
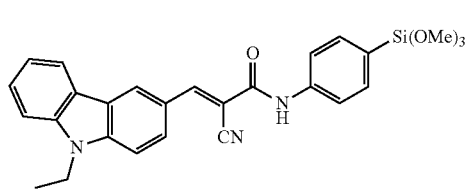
No. 76
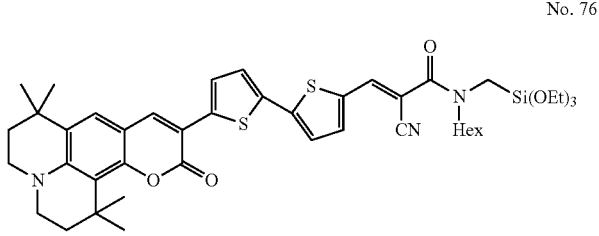
No. 77
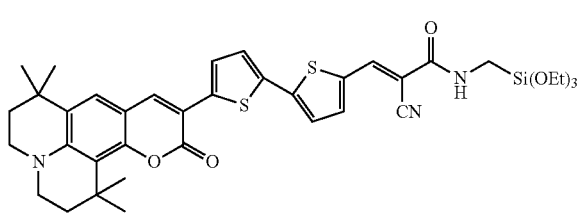
No. 78
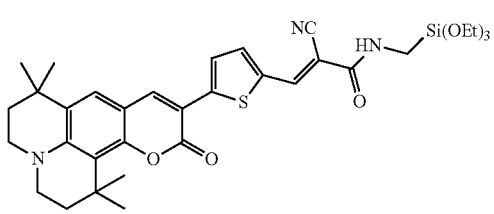
No. 79
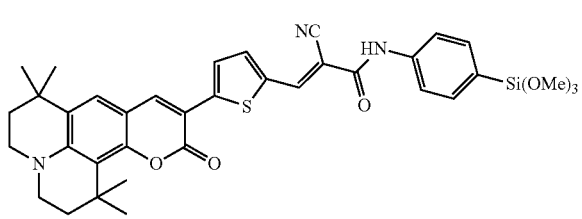
No. 80
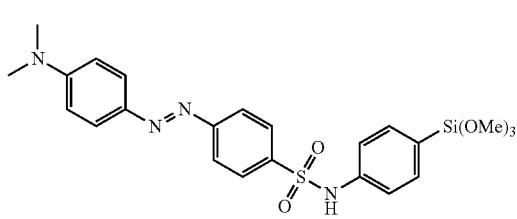

[Chemical Formula 14]
No. 81
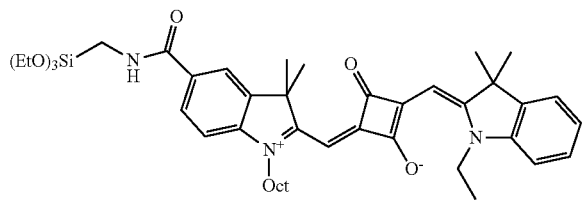
No. 82
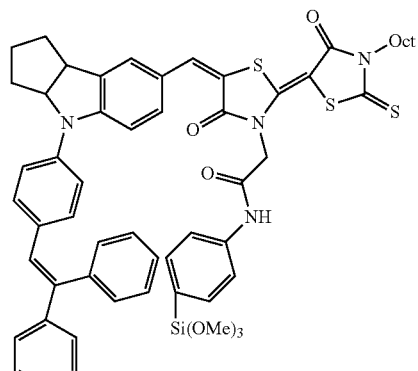
No. 83
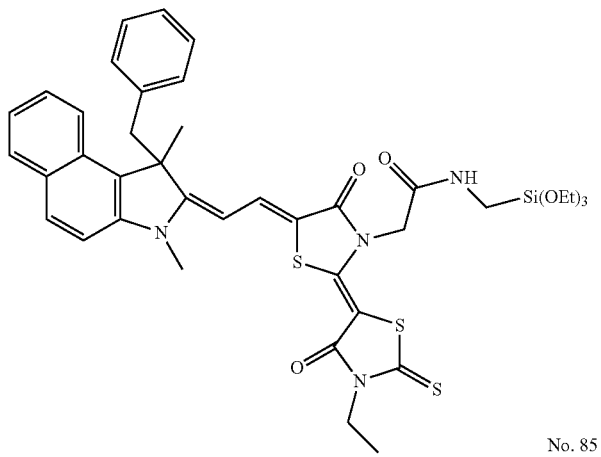
No. 84
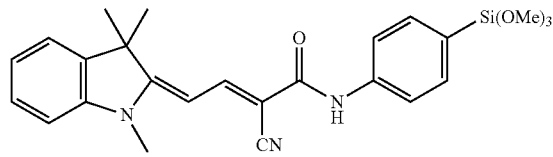
No. 85
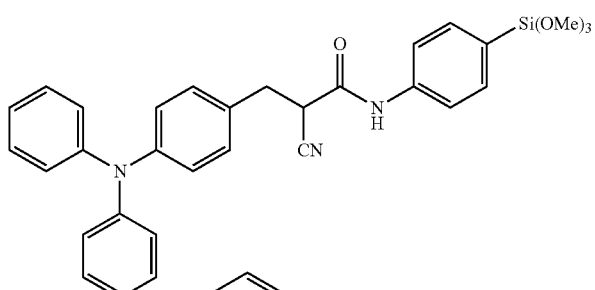
No. 86
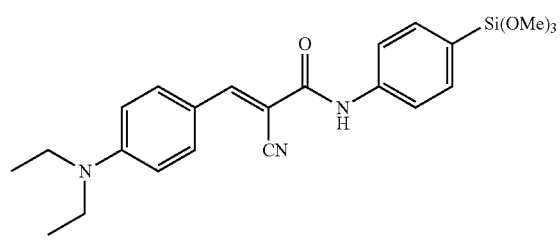
No. 87
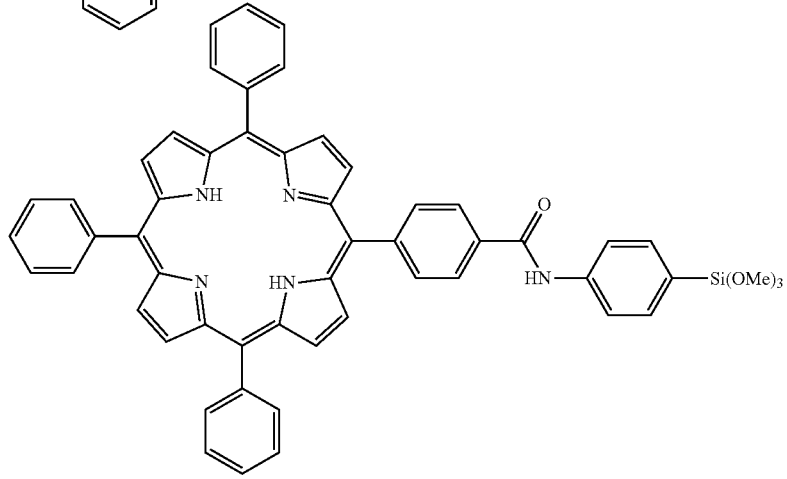

-continued
[Chemical Formula 15]
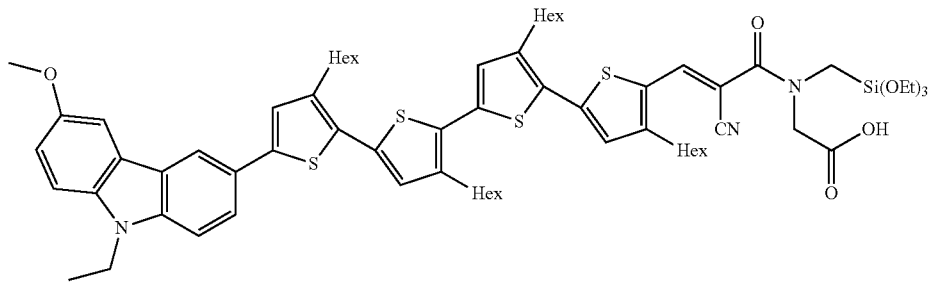
No. 88
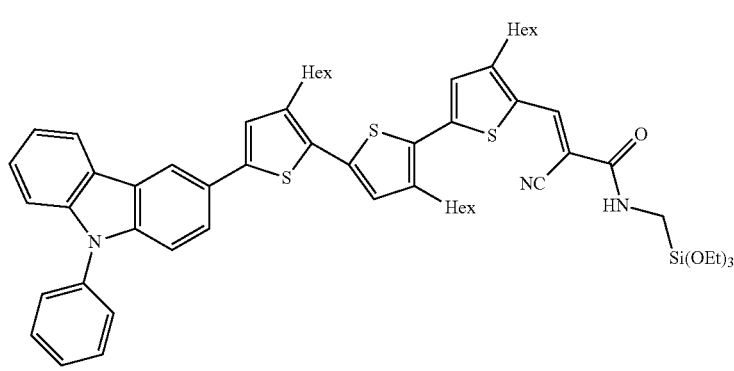
No. 89
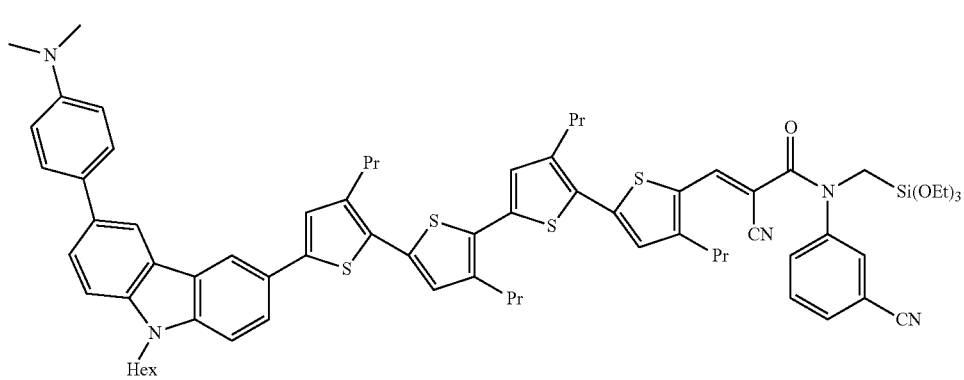
No. 90
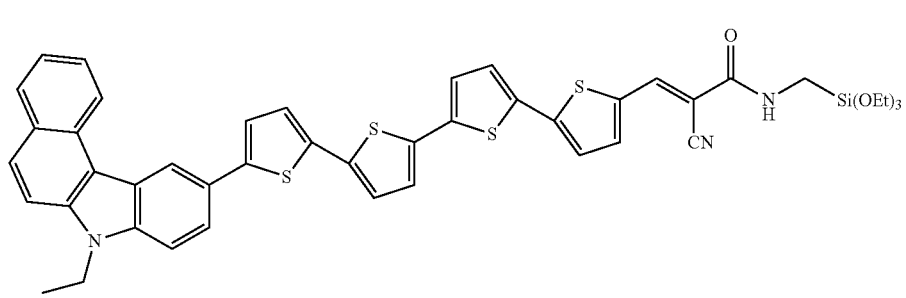
No. 91
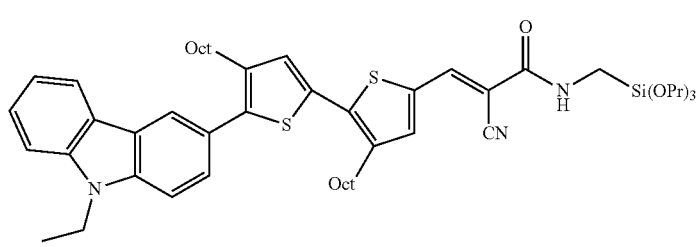
No. 92

-continued
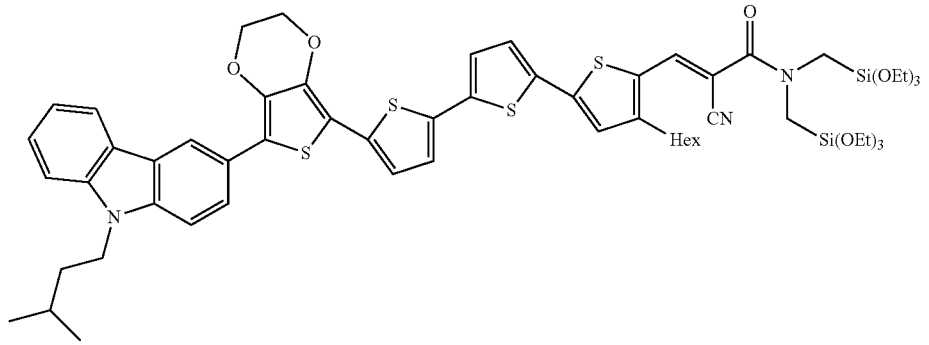
No. 93
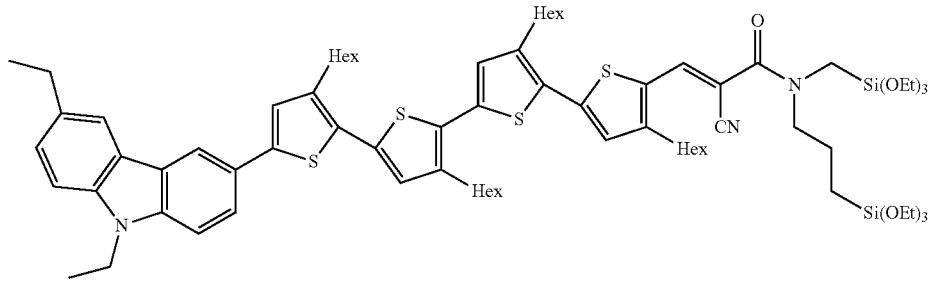
No. 94
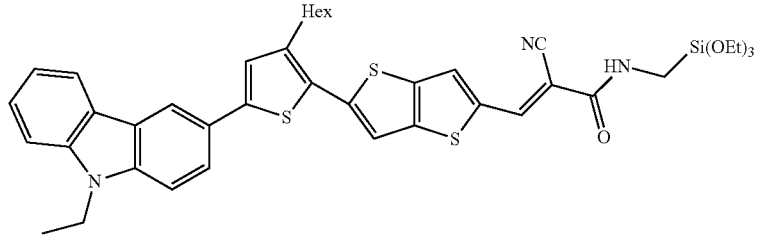
No. 95
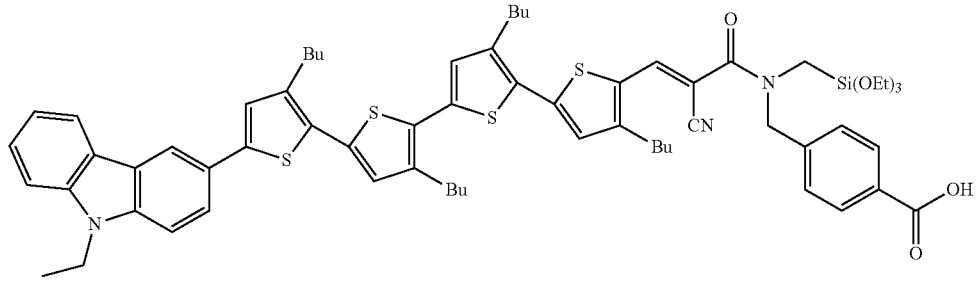
No. 96
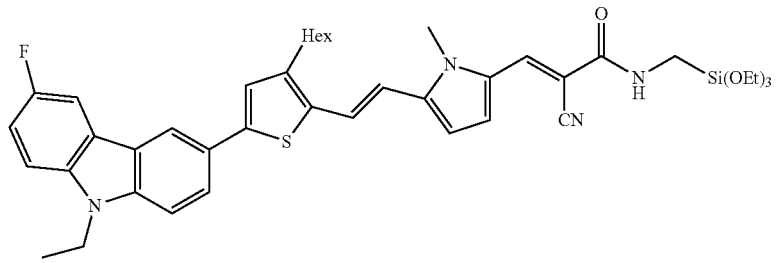
No. 97

-continued
No. 98
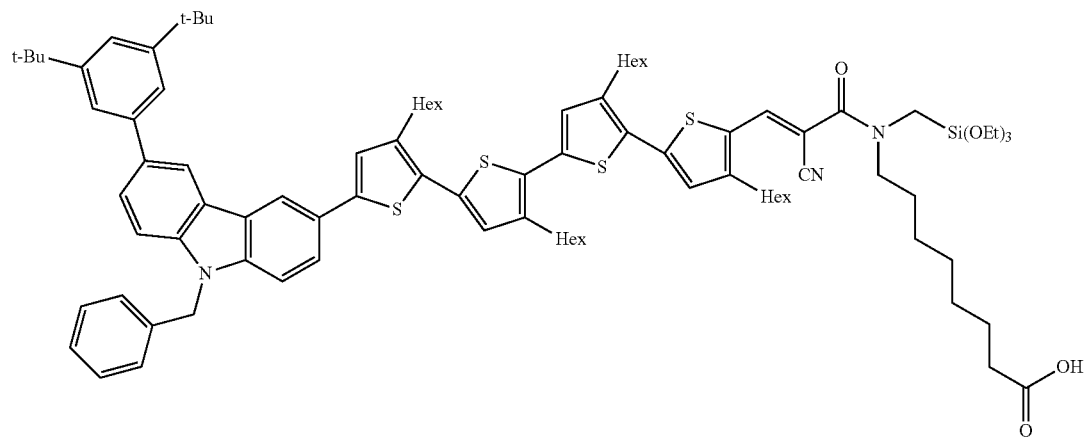
No. 99
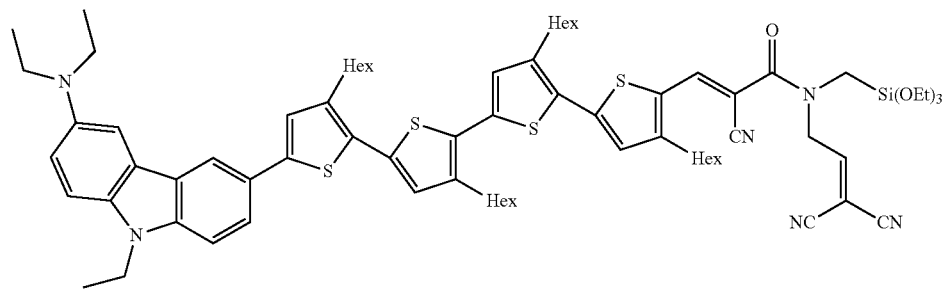
No. 100
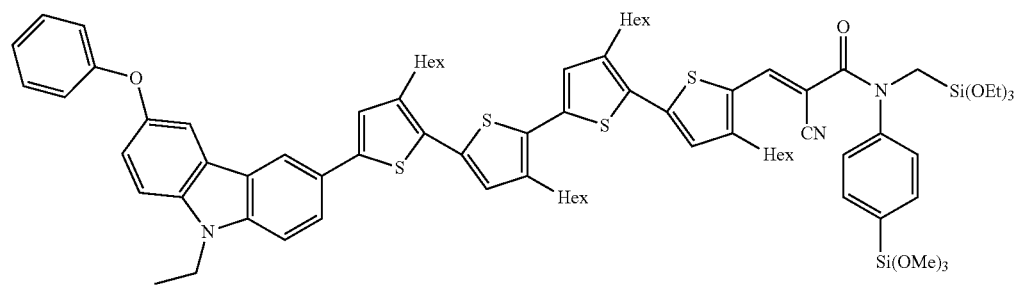
No. 101
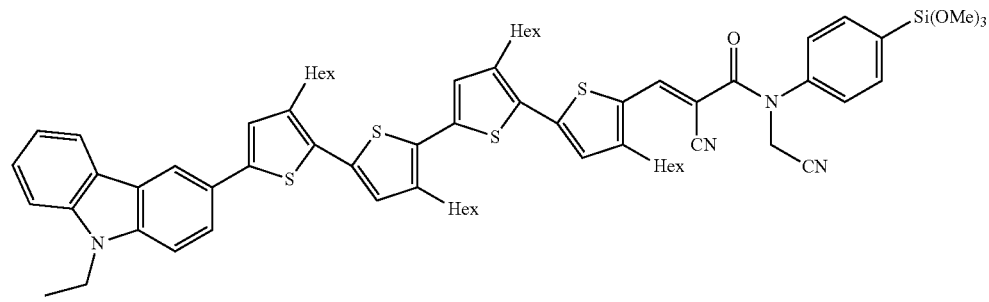
[Chemical Formula 16]
No. 102
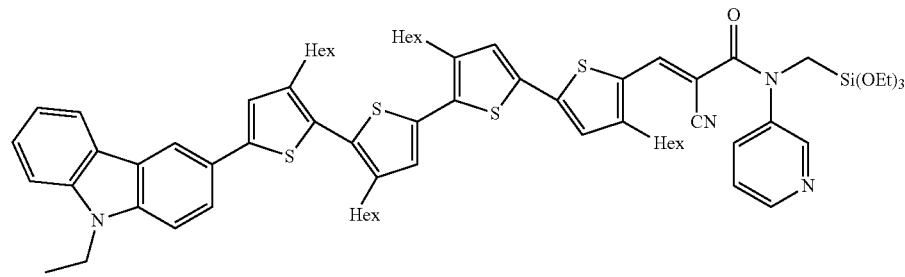

-continued
No. 103
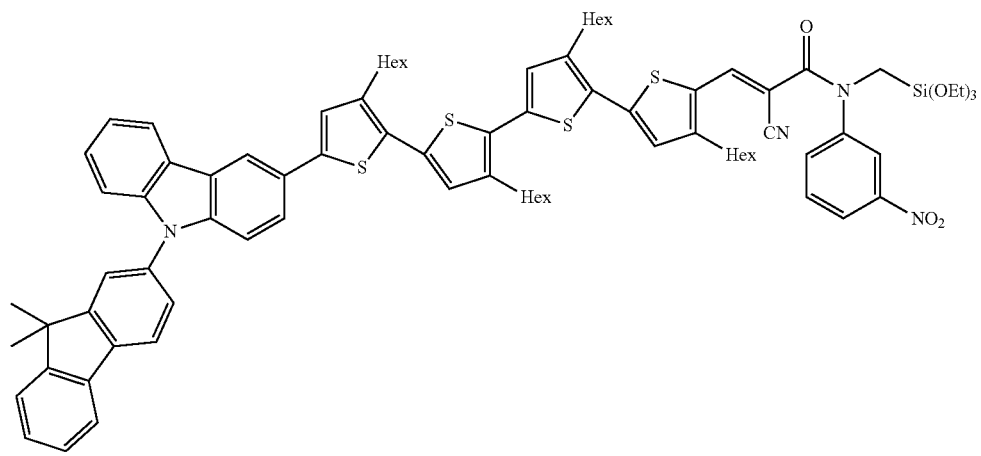
No. 104
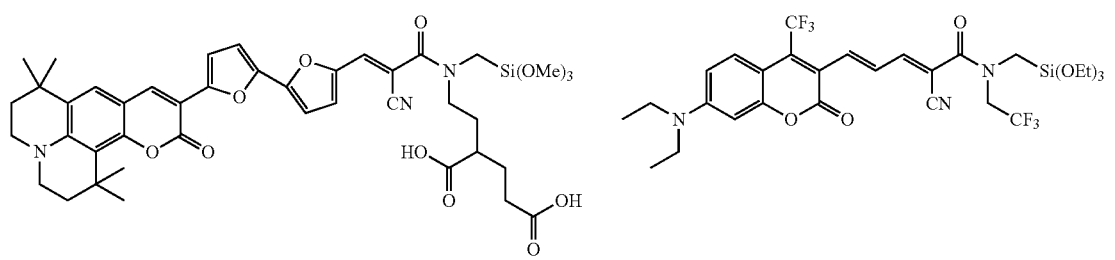
No. 105
No. 106
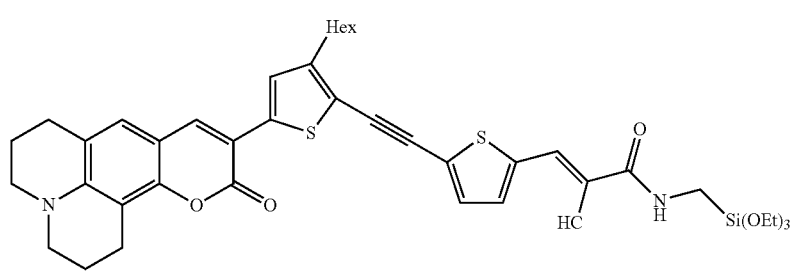
No. 107
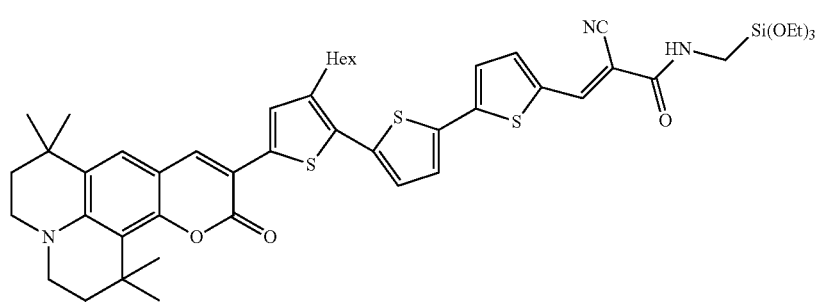
No. 108
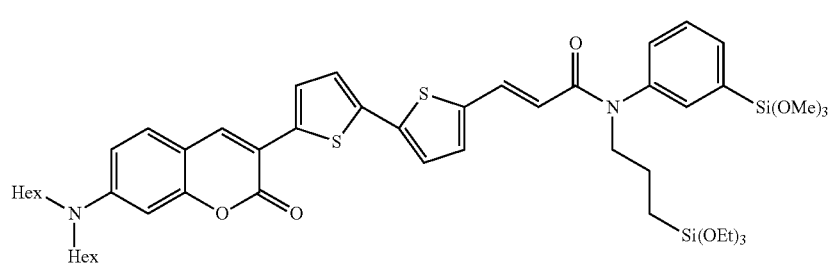

No. 109
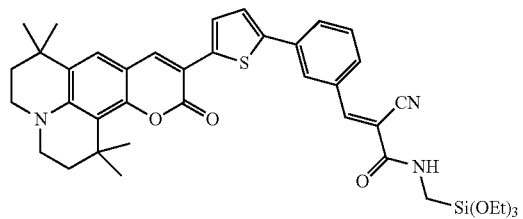
No. 110
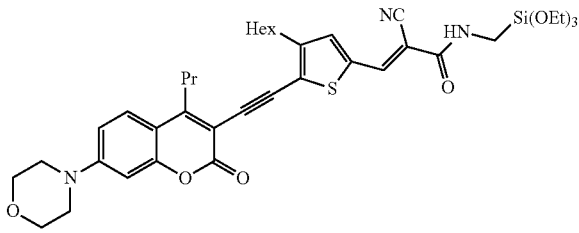
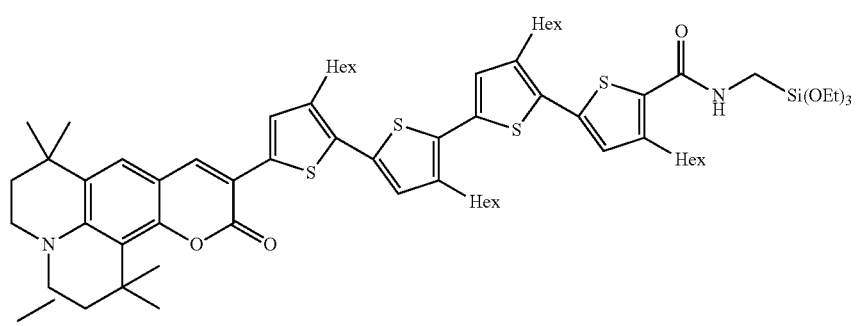
No. 111
No. 112
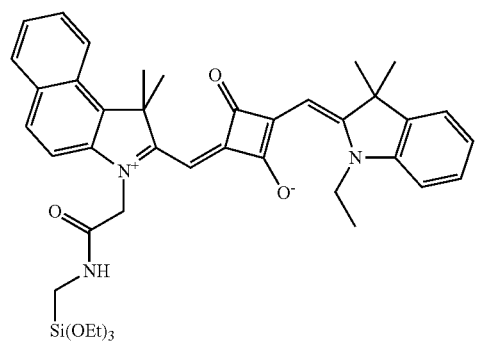
No. 113
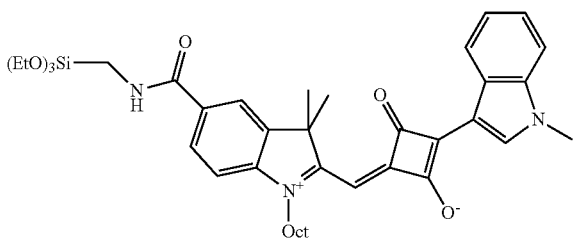
No. 114
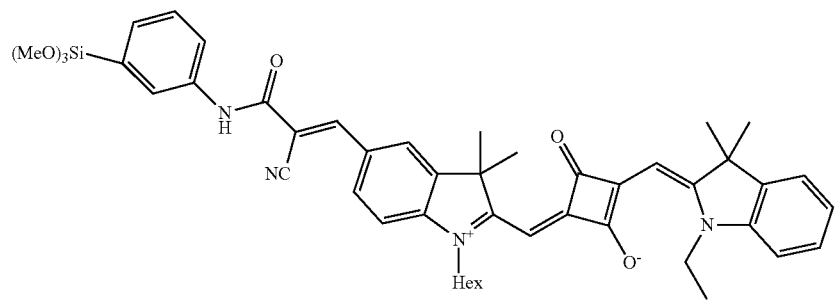

[Chemical Formula 17]
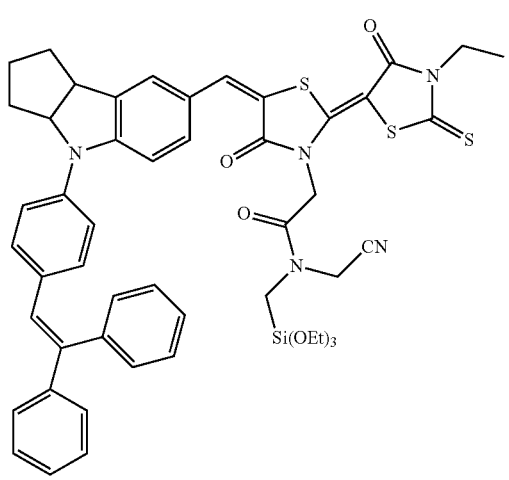
No. 115
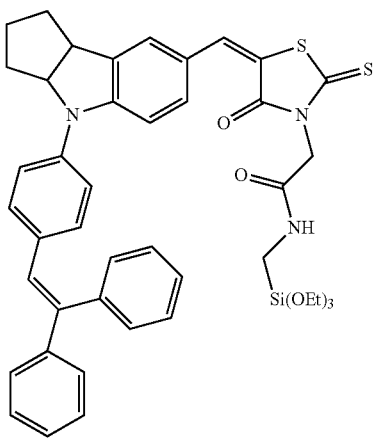
No. 116
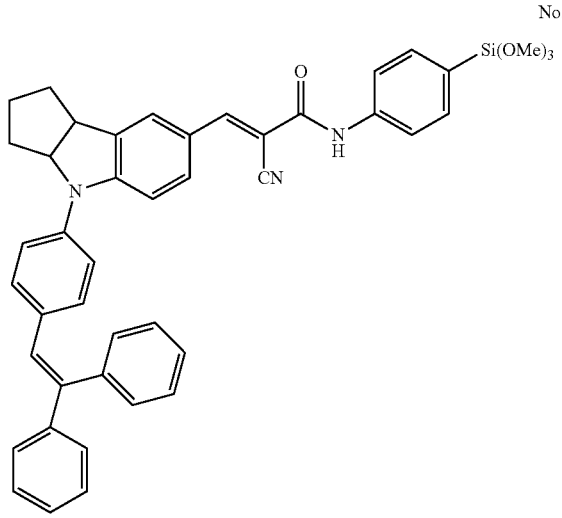
No. 117
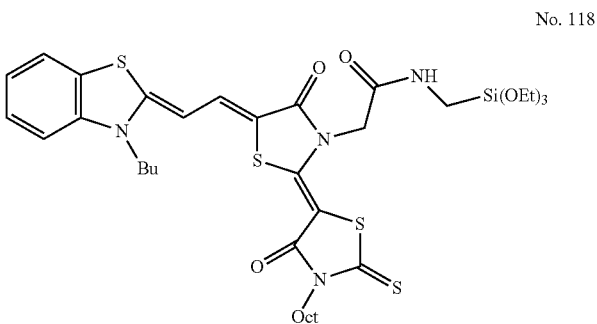
No. 118
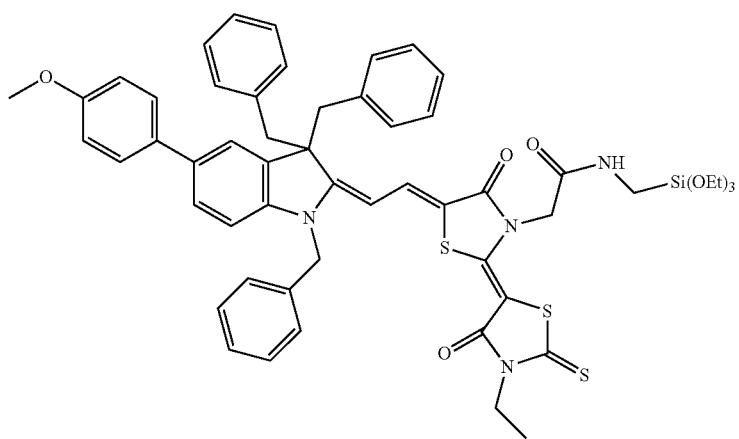
No. 119

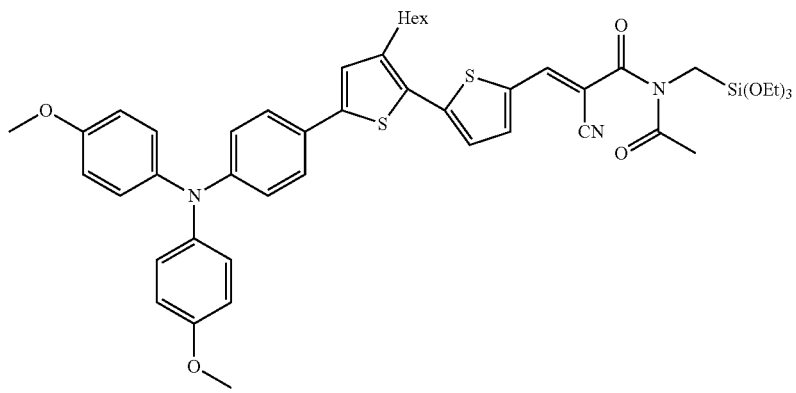
No. 120
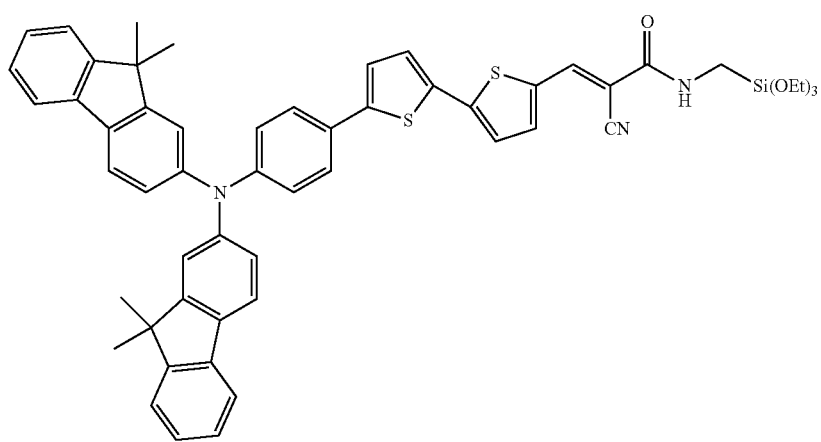
No. 121
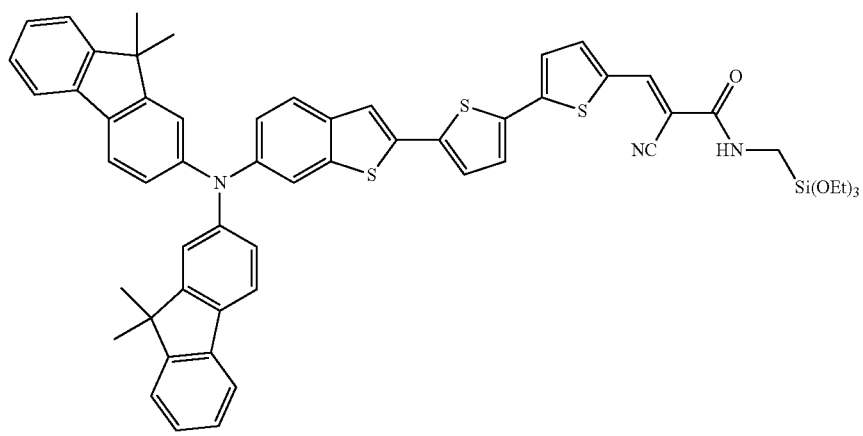
No. 122
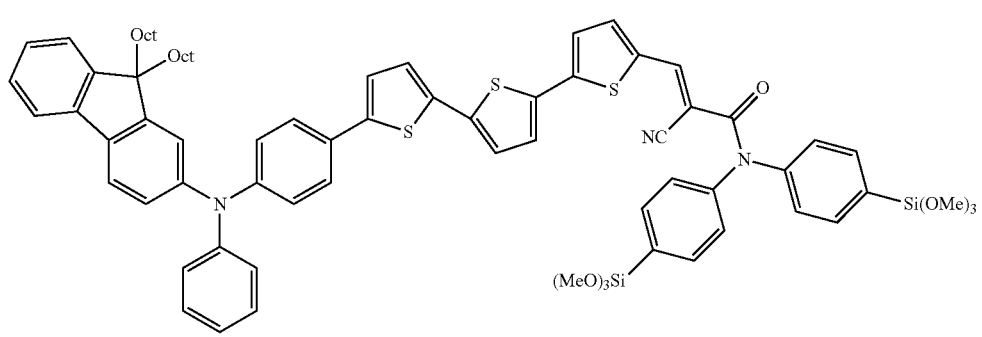
No. 123

-continued
No. 124
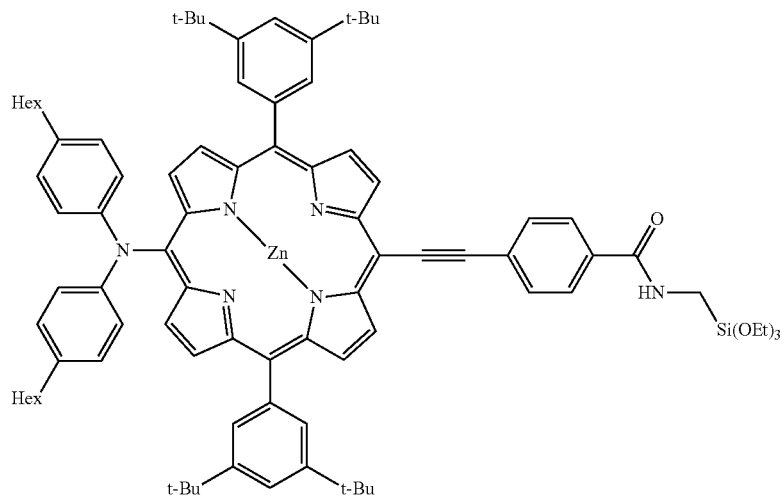
No. 125
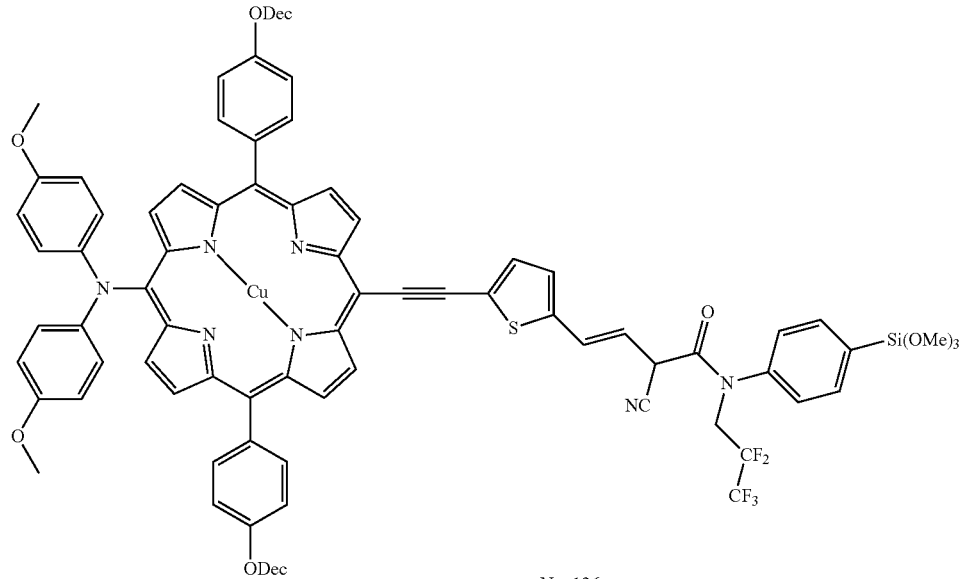
[Chemical Formula 18]
No. 126            No. 127
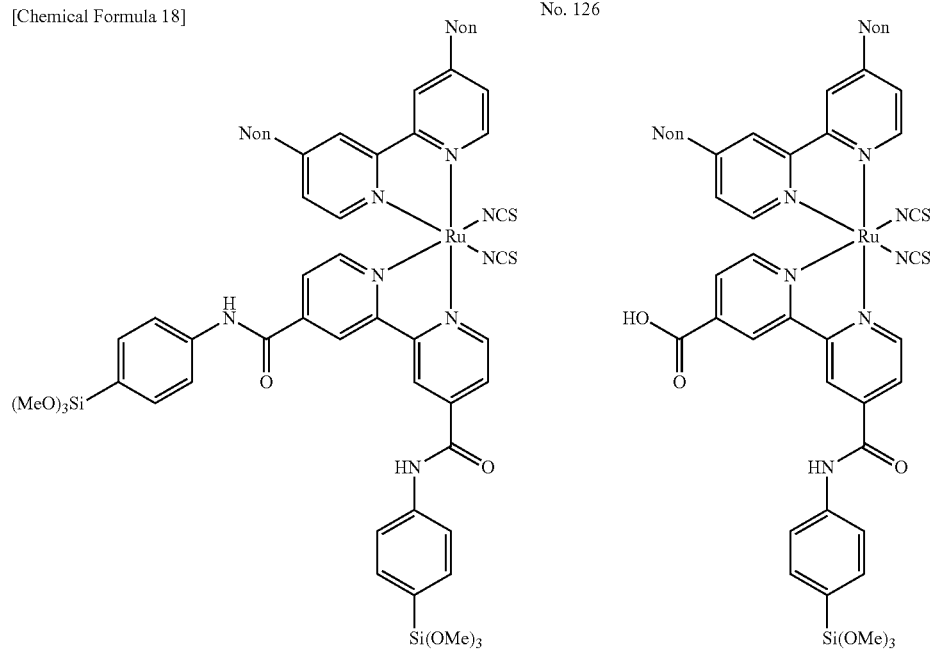

-continued
No. 128
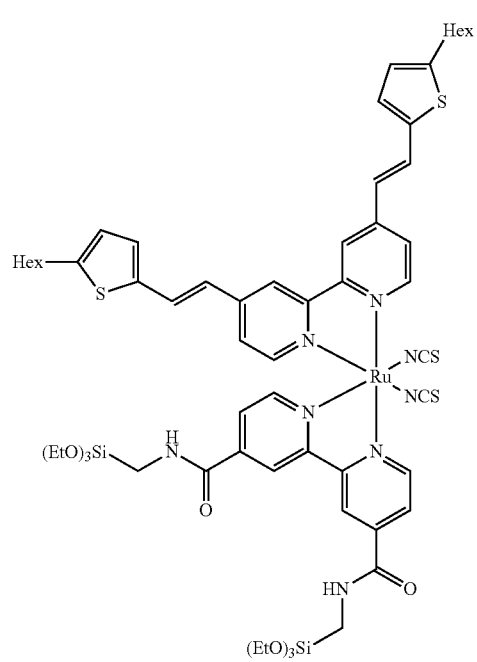
No. 129
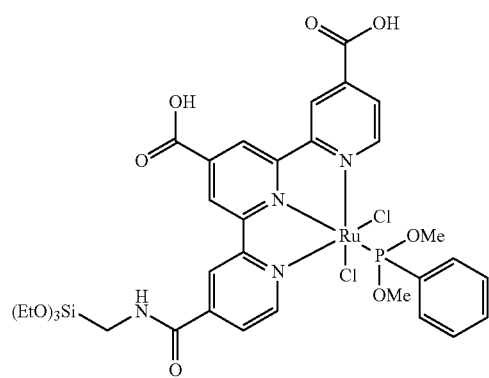
No. 130
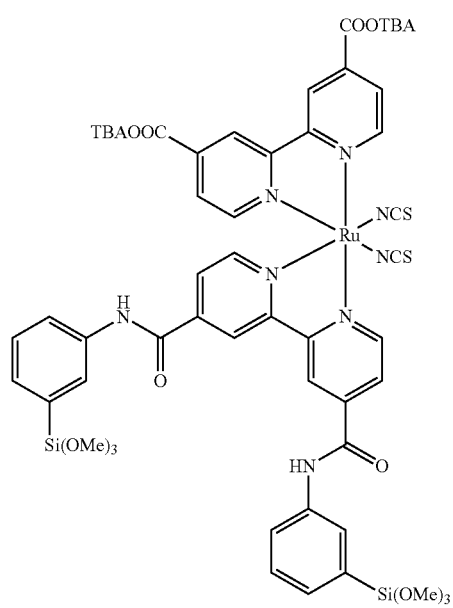
No. 131
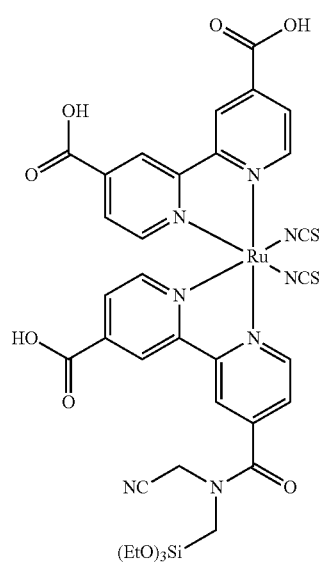

-continued
No. 132
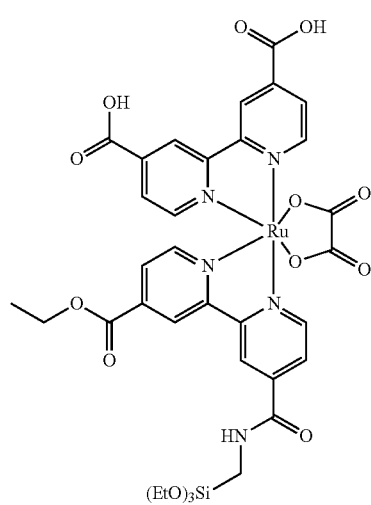
No. 133
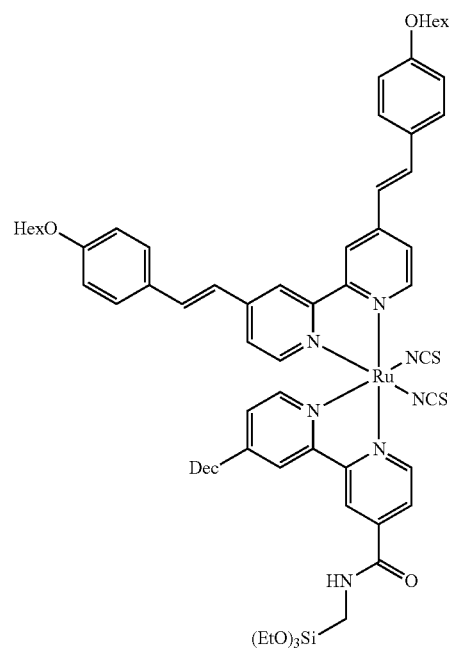
No. 134
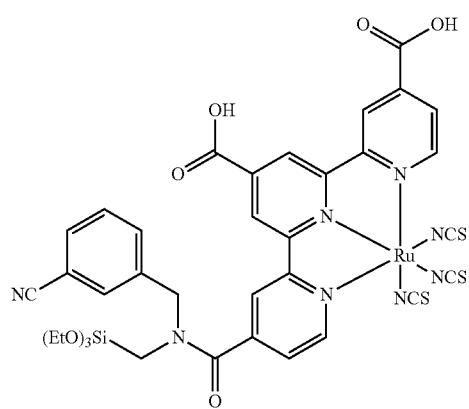
No. 135
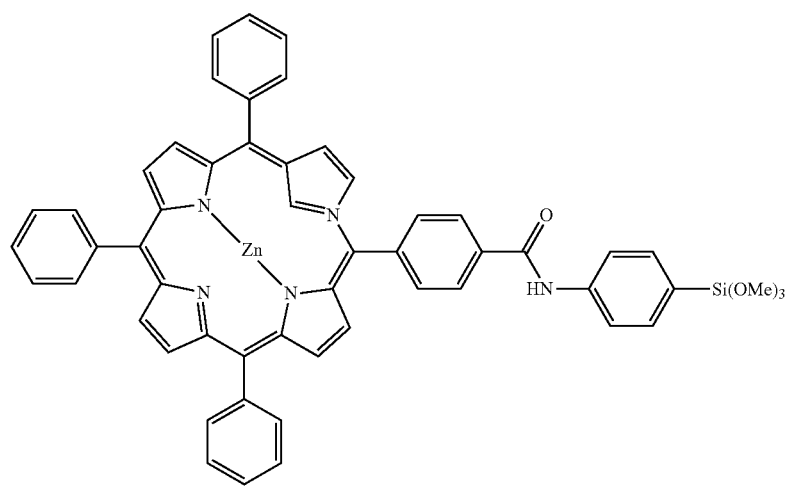

The compound represented by the above formula (1) to be used for the dye-sensitized solar cell of the present invention can be obtained by a method based on known or well-known common reactions, and the method for synthesizing it is not restricted. For example, the compound (1') in which Y in the above formula (1) is a direct bond can be obtained by making a halogen form (11) and a sililation reagent (12) react as shown in the following reaction formula (A). The catalyst, the ligand, and the base may be changed as needed.

The compounds in which Y is an optionally substituted hydrocarbon group having 1 to 20 carbon atoms and having —CO—NR$^4$— or —SO$_2$—NR$^4$— in the group can be obtained by converting a conjugated carboxylic acid having a carboxyl group into an acid chloride, and then making it react with a primary or secondary amine compound having a silyl group. The reagent to be used for the reaction may, as necessary, be altered, and that compound can be synthesized in a similar way when a sulfonic acid is used instead of a carboxylic acid.

[Chemical Formula 19]

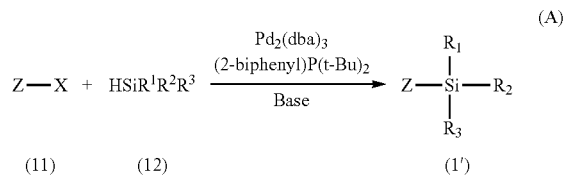

(A)

wherein Z, R$^1$, R$^2$, and R$^3$ represent the same groups as those in formula (1), X represents a halogen atom, and dba represents a dibenzylideneacetone ligand.

The dye 13 only has to include at least one compound represented by the above formula (1) and may include any other dye. Examples of any other dye include organic dyes (hereinafter referred to as other organic dyes) and organometallic complex compounds, and preferably include dyes having a group capable of adsorbing to the metal oxide semiconductor layer 12.

Examples of other organic dyes include eosin Y, dibromofluorescein, fluorescein, rhodamine B, pyrogallol, dichlorofluorescein, Erythrosine B (Erythrosine is a registered trademark), fluorescin, mercurochrome, cyanine dyes, merocyanine disazo dyes, trisazo dyes, anthraquinone dyes, polycyclic quinone dyes, indigo dyes, diphenylmethane dyes, trimethylmethane dyes, quinoline dyes, benzophenone dyes, naphthoquinone dyes, perylene dyes, fluorenone dyes, squarylium dyes, azulenium dyes, perinone dyes, quinacridone dyes, metal-free phthalocyanine dyes, metal-free porphyrin dyes, or metal-free azaporphyrin dyes.

Examples of organometallic complex compounds include organometallic complex compounds having both an ionic coordinate bond, which is formed between a metal cation and a nitrogen anion in an aromatic heterocyclic ring, and a nonionic coordinate bond, which is formed between a metal cation and a nitrogen atom or a chalcogen atom; and organometallic complex compounds having both an ionic coordinate bond, which is formed between a metal cation and an oxygen anion or a sulfur anion, and a nonionic coordinate bond, which is formed between a metal cation and a nitrogen atom or a chalcogen atom. Specific examples include metal phthalocyanine dyes such as copper phthalocyanine, titanyl phthalocyanine, cobalt phthalocyanine, nickel phthalocyanine, and iron phthalocyanine; metal naphthalocyanine dyes, metal porphyrin dyes, metal azaporphyrin dyes; and bipyridyl, terpyridyl, phenanthroline, bicinchoninate, azo, or quinolinol metal complexes with ruthenium, iron, or osmium, and other ruthenium complexes.

In addition to the above dye, the dye 13 may also contain one or more additives. Examples of such additives include association inhibitors capable of inhibiting the association of compounds in the dye, such as cholic acid compounds represented by chemical formula (13). Any of such additives may be used alone or in mixture of two or more.

[Chemical Formula 20]

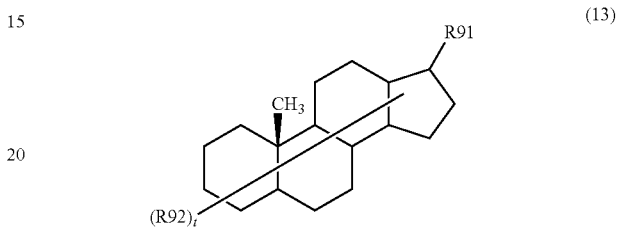

wherein R$^{91}$ represents an alkyl group having an acidic group or an alkoxysilyl group, R$^{92}$ represents a group bonded to any of the carbon atoms of the steroid skeleton and selected from a hydroxyl group, a halogen group, an alkyl group, an alkoxy group, an aryl group, a heterocyclic group, an acyl group, an acyloxy group, an oxycarbonyl group, an oxo group, an acidic group, an alkoxysilyl group, or a derivative of any of these groups, R$^{92}$ groups may be the same or different, t represents an integer of 1 to 5, and any carbon-carbon bond in the steroid skeleton may be a single bond or a double bond.

Next, description is made to the counter electrode 20. For example, the counter electrode 20 includes a conductive substrate 21 and a conductive layer 22 provided on the substrate 21. The counter electrode 20 functions as a positive electrode for the external circuit. Examples of the material for the conductive substrate 21 may include those for the substrate 11A of the conductive substrate 11 in the working electrode 10. The conductive layer 22 includes one or more conductive materials and optionally a binder. For example, the conductive material used to form the conductive layer 22 may be a metal such as platinum, gold, silver, copper (Cu), rhodium (Rh), ruthenium (Ru), aluminum (Al), magnesium (Mg), or indium (In), carbon (C), or a conductive polymer. For example, the binder that may be used to form the conductive layer 22 may be acrylic resin, polyester resin, phenolic resin, epoxy resin, cellulose, melamine resin, fluoroelastomer, or polyimide resin. Alternatively, for example, the counter electrode 20 may be a monolayer structure of the conductive layer 22.

Next, description is made to the electrolyte-containing layer 30. The electrolyte-containing layer 30 in the dye-sensitized solar cell of the present invention is not particularly restricted as long as it contains a basic compound such as a pyridine compound (JP 2003-331936 A) for improving the photoelectric conversion device in generating efficiency, durability, etc., and publicly known electrolytes (electrolytic solutions) can be used. Examples of preferred basic compounds include pyridine derivatives, imidazole derivatives, or guanidine salts. Of these derivatives and salts, examples of specific basic compounds to be used particularly preferably include 4-tert-butyl pyridine (TBP), pyridine, N-methylbenzimidazole (NMB), guanidine thiocyanate (GuSCN), 1-propyl-2,3-dimethylimidazolium iodide (DMPII), 1-propyl-3-methylimidazolium iodide (PMII), and 4-trimethylsilylpyridine (TMSP).

The electrolyte-containing layer to be used for the present invention is configured to contain a redox electrolyte having a redox couple, and examples of the redox electrolyte include an $I^-/I_3^-$ system, a $Br^-/Br_3^-$ system, a quinone/hydroquinone system, a Co complex system, a nitroxy radical compound system, a Cu complex system, and a thiolate/disulfide complex system. More specifically, the redox electrolyte may be a combination of a halide salt and elementary halogen, such as a combination of an iodide salt and elementary iodine or a combination of a bromide salt and elementary bromine. Examples of such a halide salt include cesium halide, quaternary alkyl ammonium halides, imidazolium halides, thiazolium halides, oxazolium halides, quinolinium halides, or pyridinium halides. Of these, specific examples of the iodide salt include cesium iodide; quaternary alkylammonium iodides such as tetraethylammonium iodide, tetrapropylammonium iodide, tetrabutylammonium iodide, tetrapentylammonium iodide, tetrahexylammonium iodide, tetraheptylammonium iodide, and trimethylphenylammonium iodide; imidazolium iodides such as 3-methylimidazolium iodide and 1-propyl-2,3-dimethylimidazolium iodide; thiazolium iodides such as 3-ethyl-2-methyl-2-thiazolium iodide, 3-ethyl-5-(2-hydroxyethyl)-4-methylthiazolium iodide, and 3-ethyl-2-methylbenzothiazolium iodide; oxazolium iodides such as 3-ethyl-2-methyl-benzooxazolium iodide; quinolinium iodides such as 1-ethyl-2-methylquinolinium iodide; and pyridinium iodides. Examples of the bromide salts include quaternary alkyl ammonium bromide. The combination of a halide salt and elementary halogen is preferably a combination of at least one of the above iodide salts and elementary iodine.

Alternatively, for example, the redox electrolyte may a combination of an ionic liquid and elementary halogen. In this case, the redox electrolyte may further contain the halide salt or the like. Examples of the ionic liquid include those capable of being used in batteries or solar cells, such as those disclosed in publications for example Inorg. Chem. (1996), 35, pp. 1168-1178, Electrochemistry (2002), 2, pp. 130-136, JP H09-507334 A, or JP H08-259543 A. In particular, the ionic liquid is preferably a salt having a melting point lower than room temperature (25° C.) or a salt that can be liquefied at room temperature when dissolved with any other molten salt or the like although it has a melting point higher than room temperature. Examples of the ionic liquid include the anions and the cations shown below.

Examples of ionic liquid cations include ammonium, imidazolium, oxazolium, thiazolium, oxadiazolium, triazolium, pyrrolidinium, pyridinium, piperidinium, pyrazolium, pyrimidinium, pyrazinium, triazinium, phosphonium, sulfonium, carbazolium, indolium, or a derivative of any of the above. Any of these cations may be used alone or in mixture of two or more. Specific examples include 1-methyl-3-propylimidazolium, 1-butyl-3-methylimidazolium, 1,2-dimethyl-3-propylimidazolium, and 1-ethyl-3-methylimidazolium.

Examples of ionic liquid anions include metal chlorides such as $AlCl_4^-$ and $Al_2Cl_7^-$, fluorine-containing ions such as $PF_6^-$, $BF_4^-$, $CF_3SO_3^-$, $N(CF_3SO_2)_2^-$, $F(HF)_n^-$, and $CF_3COO^-$, fluorine-free compound ions such as $NO_3^-$, $CH_3COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, and $SCN^-$, and halide ions such as iodide ions, and bromide ions. Any of these cations may be used alone or in mixture of two or more. In particular, the ionic liquid anion is preferably an iodide ion.

The electrolyte-containing layer 30 may comprise a liquid electrolyte (electrolytic solution), which is a solution of the redox electrolyte in a solvent, or may comprise a solid polymer electrolyte including an electrolytic solution held in a polymer material. Alternatively, the electrolyte-containing layer 30 may comprise a solidified (paste-like) electrolyte including a mixture of an electrolytic solution and a particulate carbon material such as carbon black. The carbon material-containing solidified electrolyte does not need to contain elementary halogen because the carbon material has the function of catalyzing the redox reaction. Such a redox electrolyte may contain one or more organic solvents in which the halide salt, the ionic liquid, or the like is soluble. Such an organic solvent may be an electrochemically inert organic solvent, such as acetonitrile, propionitrile, butyronitrile, methoxyacetonitrile, 3-methoxypropionitrile, valeronitrile, dimethyl carbonate, ethyl methyl carbonate, ethylene carbonate, propylene carbonate, N-methylpyrrolidone, pentanol, quinoline, N,N-dimethylformamide, gamma-butyrolactone, dimethyl sulfoxide, 3-methyl-1-propylimidazolium iodide, or 1,4-dioxane. Of these organic solvents, 3-methoxypropionitrile, propylene carbonate, or 3-methyl-1-propylimidazolium iodide is preferred in that it gives a high effect of the present invention.

For improving the photoelectric conversion device in generating efficiency, durability, etc., the electrolyte-containing layer 30 may also contain an additive such as an acyclic sugar (JP 2005-093313 A), a urea derivative (JP 2003-168493 A), a layered clay mineral (JP 2007-531206 T), etc. in addition to the basic compound used in the present invention.

The dye-sensitized solar cell of the present invention can be produced as described below, for example.

The working electrode 10 is first formed. The metal oxide semiconductor layer 12 having a porous structure is first formed on the conductive layer 11B-side surface of the conductive substrate 11 using an electrolytic deposition technique or a firing technique. When the metal oxide semiconductor layer 12 is formed using an electrolytic deposition technique, for example, an electrolyte bath containing a metal salt for forming a metal oxide semiconductor material is set to a predetermined temperature while the electrolyte bath is bubbled with oxygen or air, and the conductive substrate 11 is immersed in the electrolyte bath when a constant voltage is applied between the conductive substrate 11 and a counter electrode. In this process, the metal oxide semiconductor material is deposited on the conductive layer 11B so as to form a porous structure. In this process, the counter electrode may be shifted as needed in the electrolyte bath. When the metal oxide semiconductor layer 12 is formed using a firing technique, for example, a metal oxide slurry, which is prepared by dispersing a powder of a metal oxide semiconductor material in a dispersion medium, is applied to the conductive substrate 11, dried, and then fired to form a porous structure. Subsequently, a dye solution in which the dye 13 containing the compound represented by the above formula (1) is dissolved in an organic solvent is prepared. The conductive substrate 11 with the metal oxide semiconductor layer 12 formed thereon is immersed in the dye solution so that the dye 13 is deposited (supported) on the metal oxide semiconductor layer 12.

The concentration of the dye 13 in the dye solution is preferably from $1.0 \times 10^{-5}$ to $1.0 \times 10^{-3}$ mol/dm$^3$, more preferably $5.0 \times 10^{-5}$ to $5.0 \times 10^4$ mol/dm$^3$. The solvent used to form the dye solution may be of any type capable of dissolving the compound represented by the above formula (1), examples of which include hydrocarbons such as toluene, benzene, and xylene; alcohols such as methanol, ethanol, and tert-butanol; ether alcohols such as methyl cellosolve, ethyl cellosolve, butyl cellosolve, and butyl diglycol; ketones such as acetone, methyl ethyl ketone, methyl isobutyl ketone, cyclohexanone, and diacetone alcohol; esters such as ethyl acetate, butyl acetate, and methoxyethyl acetate; acrylic esters such as ethyl acrylate and butyl acrylate; fluorinated alcohols such as 2,2,3,3-tetrafluoropropanol; chlorinated hydrocarbons such as methylene dichloride, dichloroethane, and chloroform; and acetonitrile. Any of these organic solvents may be mixed together as desired. Toluene and acetonitrile are preferred.

Subsequently, the conductive layer 22 is formed on one side of the conductive substrate 21 to form the counter electrode 20. For example, the conductive layer 22 is formed by sputtering of a conductive material.

Figure 1:
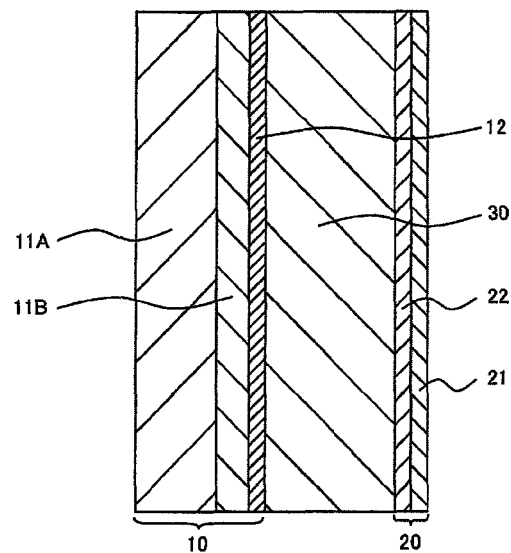
FIG. 1 is a schematic diagram showing a cross-sectional configuration in one example of the conventional dye-sensitized solar cells.

Finally, the dye 13-carrying surface of the working electrode 10 and the conductive layer 22-side surface of the counter electrode 20 are opposed to each other with a predetermined distance kept therebetween, and are fixed with a spacer (not shown) such as a sealant. Then, the whole is sealed, for example, except for the inlet for the electrolyte. Subsequently, the electrolyte is injected between the working electrode 10 and the counter electrode 20, and then the inlet is sealed, so that the electrolyte-containing layer 30 is formed. Thus, the dye-sensitized solar cell shown in FIGS. 1 and 2 is completed.

In the dye-sensitized solar cell of the present invention, the dye 13 contains the compound represented by the above formula (1), and thus the dye 13 is prevented from leaching into the electrolyte-containing layer 30 from the support material (metal oxide semiconductor layer 12) carrying the dye 13, in contrast to cases where compounds other than that compound are used. Thus, the amount of the dye 13 supported on the metal oxide semiconductor layer 12 will not decrease, so that the amount of electrons injected from the dye 13 into the metal oxide semiconductor layer 12 will not decrease. By such an effect, the durability and the conversion efficiency, especially the durability, of the dye-sensitized solar cell of the present invention can be enhanced.

Although the photoelectric conversion device described above has the electrolyte-containing layer 30 between the working electrode 10 and the counter electrode 20, the electrolyte-containing layer 30 may be replaced by a solid charge-transfer layer. In this case, like the electrolyte-containing layer 30, the solid charge-transfer layer contains a basic compound. Examples of the basic compound include those provided above as examples of the basic compound contained in the electrolyte-containing layer 30. Moreover, the solid charge-transfer layer has, for example, a solid material in which carrier transport takes part in electrical conduction. Such a material is preferably an electron transport material, a hole transport material, or the like.

The hole transport material is preferably an aromatic amine or a triphenylene derivative. Examples of the hole transport material include organic conductive polymers such as oligothiophene compounds, polypyrrole, polyacetylene or derivatives thereof, poly(p-phenylene) or derivatives thereof, polyp-phenylenevinylene) or derivatives thereof, polythienylene vinylene or derivatives thereof, polythiophene or derivatives thereof, polyaniline or derivatives thereof, and polytoluidine or derivatives thereof.

Alternatively, for example, a p-type inorganic compound semiconductor may be used as the hole transport material. The p-type inorganic compound semiconductor is preferably has a band gap of 2 eV or more, more preferably 2.5 eV or more. The p-type inorganic compound semiconductor must have an ionization potential smaller than that of the working electrode 10 to create conditions under which the holes from the dye can be reduced. Although the preferred range of the ionization potential of the p-type inorganic compound semiconductor varies with the dye used, the ionization potential is preferably in the range of 4.5 eV to 5.5 eV, more preferably in the range of 4.7 eV to 5.3 eV.

For example, the p-type inorganic compound semiconductor may be a monovalent copper compound semiconductor. Examples of the monovalent copper compound semiconductor include CuI, CuSCN, CuInSe$_2$, Cu(In,Ga)Se$_2$, CuGaSe$_2$, Cu$_2$O, CuS, CuGaS$_2$, CuInS$_2$, CuAlSe$_2$, and the like. Other examples of the p-type inorganic compound semiconductor include GaP, NiO, CoO, FeO, Bi$_2$O$_3$, MoO$_2$, Cr$_2$O$_3$, or the like.

For example, such a solid charge-transfer layer may be formed by a method of forming a solid charge-transfer layer directly on the working electrode 10, which may be followed by forming the counter electrode 20.

For example, the hole transport material including an organic conductive polymer can be introduced into the interior of the electrode by a technique such as vacuum deposition, casting, coating, spin coating, immersion, electrolytic polymerization, or photo-electrolytic polymerization. The solid inorganic compound can also be introduced into the interior of the electrode by a technique such as casting, coating, spin coating, immersion, or electroplating. Part of the solid charge-transfer layer formed as described above (especially having a hole transport material) is preferably infiltrated into part of the pores of the porous structure of the metal oxide semiconductor layer 12 so that it can be in direct contact.

The compound represented by the above formula (1) to be used for the present invention can improve durability and conversion efficiency, especially conversion efficiency, as in the case of having provided an electrolyte-containing layer 30 even in a dye-sensitized solar cell in which a solid charge-transfer layer has been provided instead of the electrolyte-containing layer 30.

EXAMPLES

Hereinafter, the present invention is more specifically described with reference to examples and comparative examples, which, however, are not intended to limit the present invention.

Example 1-1

First prepared was the conductive substrate 11 made of a 2.0 cm long, 1.5 cm wide, 1.1 mm thick conductive glass substrate (F—SnO$_2$). Subsequently, 70 μm thick masking tapes were bonded to the conductive substrate 11 so as to surround a 0.5 cm long, 0.5 cm wide square area, and 3 cm$^3$ of a metal oxide slurry was applied in uniform thickness to the square area and then dried. The metal oxide slurry used was a suspension of 10% by weight of titanium oxide powder (TiO$_2$, Ti-Nanoxide D manufactured by Solaronix SA.) in water. Subsequently, the masking tapes were peeled off from the conductive substrate 11, and the substrate was fired at 450° C. in an electric furnace, so that the metal oxide semiconductor layer 12 with a thickness of about 5 μm was formed. Subsequently, compound No. 1 was dissolved at a concentration of 3×10$^{-4}$ mol/dm$^3$ in toluene to form a dye solution. Subsequently, the conductive substrate 11 with a photocatalyst film (a metal oxide semiconductor layer) 12 formed thereon was immersed in the dye solution, so that a working electrode 10 with a dye 13 carried thereon was formed.

The formed working electrode 10 was immersed in a remover (0.5 M 4-tert-butylpyridine/acetonitrile:water=10:1) under the conditions of 25° C. and 4 hours. Table 1 shows the amount of the supported dye (the absorbance (Abs.) of the dye at λmax) after the immersion in the remover, as a measure of the resistance to removal, when the amount of the supported dye (the absorbance (Abs.) of the dye at λmax) before the immersion in the remover is normalized as 100. It can be concluded that the closer to 100 the amount of the supported dye after the removal is, the higher the resistance to removal. The remover represents an electrolyte composition containing a basic compound (4-tert-butylpyridine). The water contained in the electrolyte composition in a concentration of 10% represents a degradation accelerator that accelerates the removal of a dye.

Examples 1-2 to 1-5 and Comparative Examples 1-1 to 1-3

The working electrode 10 carrying each compound was prepared using the same process as in Example 1-1 except that compound No. 1 was replaced by the compound shown in Table 1, and the resistance of the dye to removal was determined as in Example 1-1. The results are shown in Table 1.

[Chemical Formula 21]

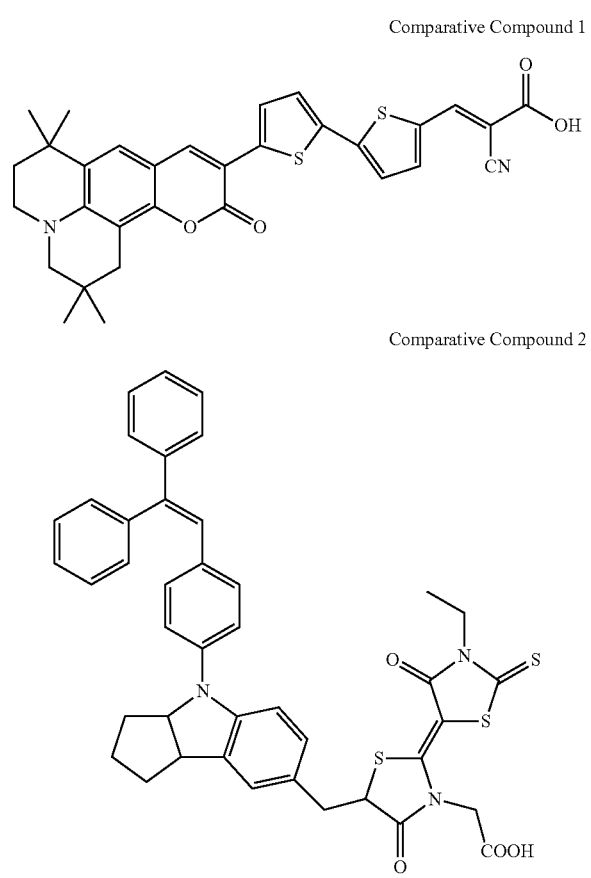

Comparative Compound 1

Comparative Compound 2

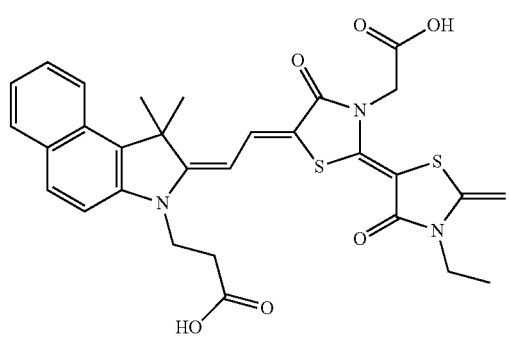

Comparative Compound 3

TABLE 1

| | Dye Compound | Resistance to Removal |
|---|---|---|
| Example 1-1 | No. 1 | 61 |
| Example 1-2 | No. 12 | 74 |
| Example 1-3 | No. 72 | 82 |
| Example 1-4 | No. 73 | 82 |
| Example 1-5 | No. 83 | 100 |
| Comparative Example 1-1 | Comparative Compound 1 | 0 |
| Comparative Example 1-2 | Comparative Compound 2 | 0 |
| Comparative Example 1-3 | Comparative Compound 3 | 25 |

Example 2-1

Two working electrodes 10 were prepared by the same procedures as used in Example 1-1. One working electrode 10 was immersed in the following remover a containing a basic compound, and the other one was immersed in the following remover a' containing no basic compounds, respectively, under the conditions of 25° C. and 4 hours. Then, removing parameters were calculated using the following formula.

Removing parameter=(remaining rate of dye in the presence of basic compound)/(remaining rate of dye in the absence of basic compound)

The larger the value of removing parameter is, the higher ability the working electrode has to retain the dye in an electrolytic solution containing a basic compound. The amount of the supported dye was determined by procedures analogous those used in Example 1-1. The result is shown in Table 3A.

<Remover a> 0.5 M 4-tert-butyl pyridine/acetonitrile:water=10:1

<Remover a'> Acetonitrile:water=10:1

Examples 2-3 to 2-34 and Comparative Examples 2-1 to 2-20

Removing parameters were calculated by the same operation as used in Example 2-1 except that the dye compound, the oxide semiconductor, or the remover was changed to that shown in [Table 2], [Table 3A], or [Table 3B]. The results are shown in [Table 3A] and [Table 3B].

TBP: 4-tert-butylpyridine
NMB: N-methylbenzimidazole
GuSCN: guanidine thiocyanate DMPII: 1-propyl-2,3-dimethylimidazolium iodide
TMSP: 4-trimethylsilylpyridine

TABLE 2

| Remover | Remover containing basic compound | Remover containing no basic compound |
|---|---|---|
| A | 0.5M TBP/acetonitrile:water = 10:1 | Acetonitrile:water = 10:1 |
| B | 0.1M TBP/acetonitrile:water = 10:1 | Acetonitrile:water = 10:1 |
| C | 1.0M TBP/acetonitrile:water = 10:1 | Acetonitrile:water = 10:1 |
| D | 0.5M Pyridine/acetonitrile:water = 10:1 | Acetonitrile:water = 10:1 |
| E | 0.5M NMB/acetonitrile:water = 10:1 | Acetonitrile:water = 10:1 |
| F | 0.1M GuSCN/acetonitrile:water = 10:1 | Acetonitrile:water = 10:1 |
| G | 0.5M DMPII/acetonitrile:water = 10:1 | Acetonitrile:water = 10:1 |
| H | 0.1M TMSP/acetonitrile:water = 10:1 | Acetonitrile:water = 10:1 |
| I | 0.5M TBP/0.1M GuSCN/acetonitrile:water = 10:1 | Acetonitrile:water = 10:1 |
| J | 0.5M TBP/3-methoxy-propionitrile:water = 10:1 | 3-Methoxy-propionitrile:water = 10:1 |
| K | 0.5M TBP/propylene carbonate:water = 10:1 | Propylene carbonate:water = 10:1 |
| L | 0.5M TBP/(acetonitrile:3-methoxypropionitrile = 1:1):water = 10:1 | 3-Methoxy-propionitrile:water = 10:1 |

TABLE 3A

| | Dye Compound | Oxide Semiconductor | Remover | Removing Parameter |
|---|---|---|---|---|
| Example 2-1 | No. 1 | TiO$_2$ | A | 1.02 |
| Example 2-2 | No. 9 | TiO$_2$ | A | 0.64 |
| Example 2-3 | No. 65 | TiO$_2$ | A | 1.12 |
| Example 2-4 | No. 66 | TiO$_2$ | A | 0.98 |
| Example 2-5 | No. 67 | TiO$_2$ | A | 1.02 |
| Example 2-6 | No. 71 | TiO$_2$ | A | 0.93 |
| Example 2-7 | No. 72 | TiO$_2$ | A | 0.90 |
| Example 2-8 | No. 73 | TiO$_2$ | A | 0.95 |
| Example 2-9 | No. 83 | TiO$_2$ | A | 1.00 |
| Example 2-10 | No. 67 | ZnO | A | 0.93 |
| Example 2-11 | No. 73 | ZnO | A | 1.01 |
| Comparative Example 2-1 | Comparative Compound 1 | TiO$_2$ | A | 0.00 |
| Comparative Example 2-2 | Comparative Compound 2 | TiO$_2$ | A | 0.00 |
| Comparative Example 2-3 | Comparative Compound 3 | TiO$_2$ | A | 0.34 |
| Comparative Example 2-4 | Comparative Compound 4 | TiO$_2$ | A | 0.49 |
| Comparative Example 2-5 | Comparative Compound 5 | TiO$_2$ | A | 0.00 |
| Comparative Example 2-6 | Comparative Compound 2 | ZnO | A | 0.53 |
| Example 2-12 | No. 66 | TiO$_2$ | B | 1.14 |
| Example 2-13 | No. 73 | TiO$_2$ | B | 0.91 |
| Comparative Example 2-7 | Comparative Compound 2 | TiO$_2$ | B | 0.00 |
| Comparative Example 2-8 | Comparative Compound 4 | TiO$_2$ | B | 0.69 |
| Example 2-14 | No. 66 | TiO$_2$ | C | 1.02 |
| Example 2-15 | No. 73 | TiO$_2$ | C | 0.99 |
| Comparative Example 2-9 | Comparative Compound 2 | TiO$_2$ | C | 0.00 |
| Comparative Example 2-10 | Comparative Compound 4 | TiO$_2$ | C | 0.39 |

TABLE 3B

| | Dye Compound | Oxide Semiconductor | Remover | Removing Parameter |
|---|---|---|---|---|
| Example 2-16 | No. 9 | TiO$_2$ | D | 0.92 |
| Example 2-17 | No. 12 | TiO$_2$ | D | 1.18 |
| Example 2-18 | No. 65 | TiO$_2$ | D | 1.10 |
| Example 2-19 | No. 66 | TiO$_2$ | D | 1.32 |
| Example 2-20 | No. 83 | TiO$_2$ | D | 1.18 |
| Comparative Example 2-11 | Comparative Compound 2 | TiO$_2$ | D | 0.04 |
| Example 2-21 | No. 9 | TiO$_2$ | E | 0.96 |
| Example 2-22 | No. 12 | TiO$_2$ | E | 1.12 |
| Example 2-23 | No. 65 | TiO$_2$ | E | 1.18 |
| Example 2-24 | No. 66 | TiO$_2$ | E | 1.48 |
| Example 2-25 | No. 67 | TiO$_2$ | E | 1.00 |
| Comparative Example 2-12 | Comparative Compound 2 | TiO$_2$ | E | 0.00 |
| Example 2-26 | No. 65 | TiO$_2$ | F | 0.99 |
| Example 2-27 | No. 67 | TiO$_2$ | F | 0.95 |
| Comparative Example 2-13 | Comparative Compound 2 | TiO$_2$ | F | 0.41 |
| Example 2-28 | No. 66 | TiO$_2$ | G | 2.08 |
| Comparative Example 2-14 | Comparative Compound 2 | TiO$_2$ | G | 0.39 |
| Example 2-29 | No. 66 | TiO$_2$ | H | 1.10 |
| Example 2-30 | No. 73 | TiO$_2$ | H | 1.01 |
| Comparative Example 2-15 | Comparative Compound 2 | TiO$_2$ | H | 0.17 |
| Comparative Example 2-16 | Comparative Compound 4 | TiO$_2$ | H | 0.63 |
| Example 2-31 | No. 66 | TiO$_2$ | I | 1.54 |
| Comparative Example 2-17 | Comparative Compound 2 | TiO$_2$ | I | 0.00 |
| Example 2-32 | No. 66 | TiO$_2$ | J | 2.50 |
| Comparative Example 2-18 | Comparative Compound 2 | TiO$_2$ | J | 0.55 |
| Example 2-33 | No. 66 | TiO$_2$ | K | 1.50 |
| Comparative Example 2-19 | Comparative Compound 2 | TiO$_2$ | K | 0.00 |
| Example 2-34 | No. 9 | TiO$_2$ | L | 0.92 |
| Comparative Example 2-20 | Comparative Compound 2 | TiO$_2$ | L | 0.00 |

[Chemical Formula 22]

Comparative Compound 4

Comparative Compound 5

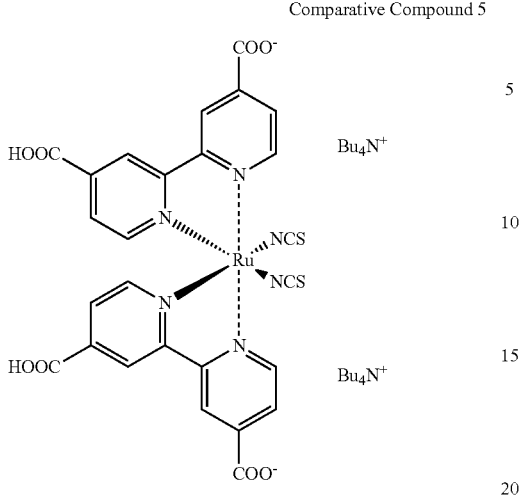

The results disclosed above clearly show that the removal of the dye compound according to the dye-sensitized solar cell of the present invention from an oxide semiconductor is suppressed even in a device using an electrolyte composition containing a basic compound.

The invention claimed is:

1. A dye-sensitized solar cell comprising a working electrode having a photocatalytic film, a counter electrode, and an electrolyte-containing layer or a solid charge-transfer layer,
wherein the dye-sensitized solar cell contains a basic compound in the electrolyte-containing layer or the solid charge-transfer layer, and
the photocatalytic film comprises an oxide semiconductor layer containing a dye compound represented by formula (1), $$Z-Y-\underset{\underset{R^3}{|}}{\overset{\overset{R^1}{|}}{Si}}-R^2 \quad (1)$$

wherein Y is any one of structural formulae (Y-1) to (Y-12)

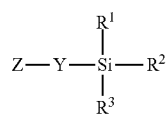 (Y-1)

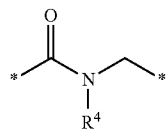 (Y-2)

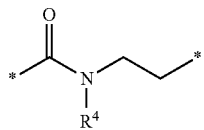 (Y-3)

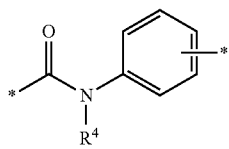

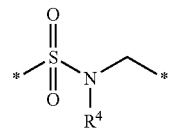 (Y-4)

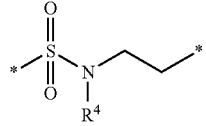 (Y-5)

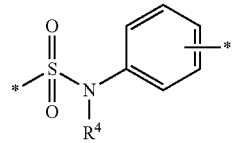 (Y-6)

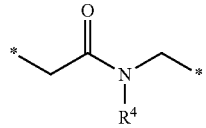 (Y-7)

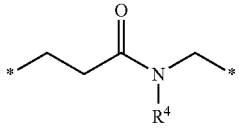 (Y-8)

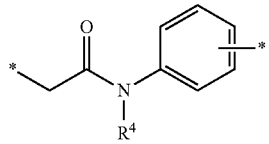 (Y-9)

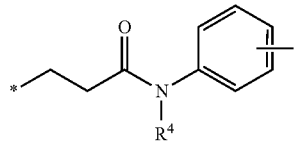 (Y-10)

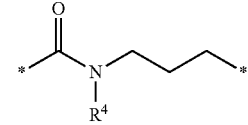 (Y-11)

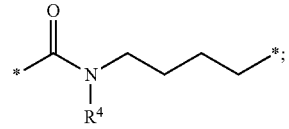 (Y-12)

Z is a conjugated group;
$R^1$, $R^2$, and $R^3$ each represent an optionally substituted hydrocarbon group or an optionally substituted hydrocarbonoxy group;
at least one of $R^1$, $R^2$, and $R^3$ is an optionally substituted hydrocarbonoxy group; and
$R^4$ represents a hydrogen atom or an optionally substituted hydrocarbon group having 1 to 20 carbon atoms.

2. The dye-sensitized solar cell according to claim 1, wherein Z in the formula (1) is represented with any one of structural formulae (2-1) to (2-5),

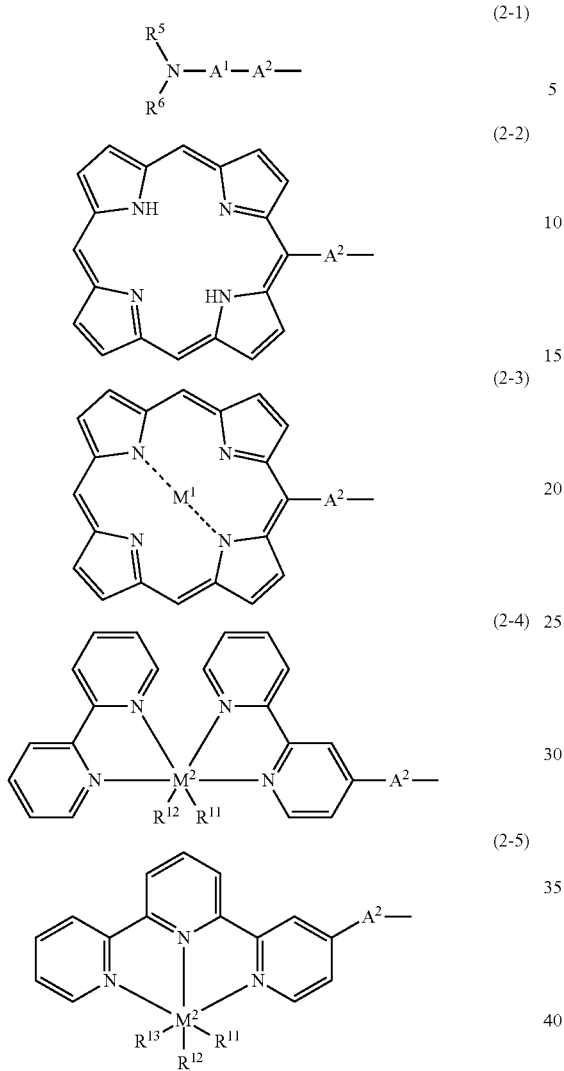

(2-1)
(2-2)
(2-3)
(2-4)
(2-5)

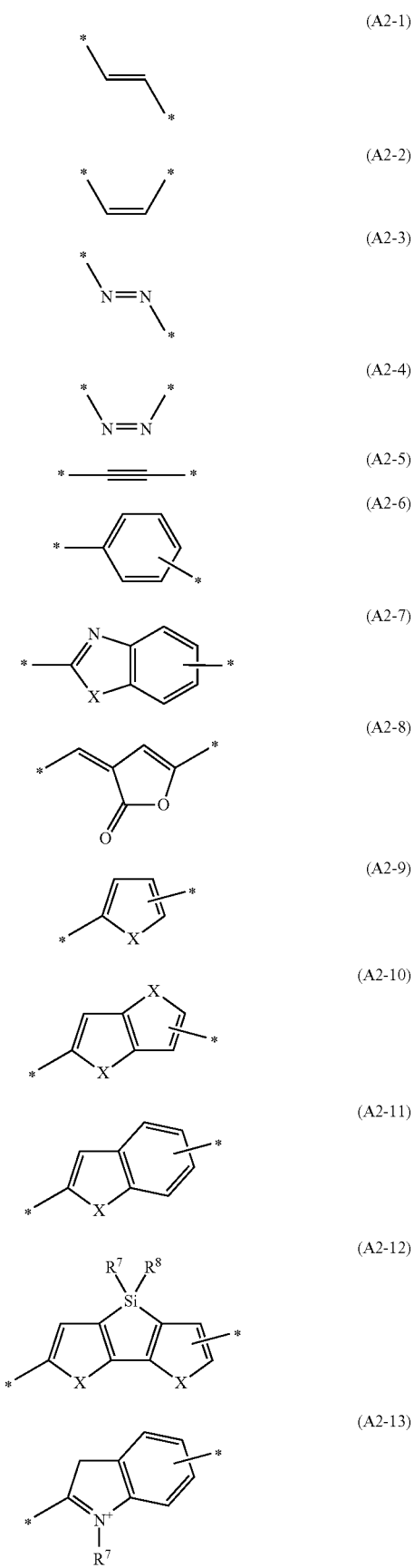

(A2-1)
(A2-2)
(A2-3)
(A2-4)
(A2-5)
(A2-6)
(A2-7)
(A2-8)
(A2-9)
(A2-10)
(A2-11)
(A2-12)
(A2-13)

wherein $A^1$ is an optionally substituted aromatic hydrocarbon ring group or an optionally substituted aromatic heterocyclic group, $A^2$ represents a direct bond or a group comprising a chain of one to seven of one or more groups selected from groups represented by formulae (A2-1) to (A2-15), $R^5$ and $R^6$ each represent an optionally substituted hydrocarbon group, $R^5$ and $R^6$ may be linked together to form a ring, and $R^5$ and $R^6$ may be each independently linked with $A^1$ to form a ring, $R^{11}$, $R^{12}$, and $R^{13}$ each represent a known ligand that coordinates to $M^2$, $M^1$ and $M^2$ each represents a metal element, any hydrogen atoms in the formulae may be substituted with a fluorine atom, a chlorine atom, an iodine atom, a bromine atom, a cyano group, a nitro group, an —$OR^2$ group, an —$SR^2$ group, an optionally substituted aliphatic hydrocarbon group, or Y—$SiR^1R^2R^3$, wherein $R^1$, $R^2$, and $R^3$ each represent an optionally substituted hydrocarbon group or an optionally substituted hydrocarbonoxy group, and $R^7$ represents a hydrogen atom or an optionally substituted hydrocarbon group, -continued (A2-14)
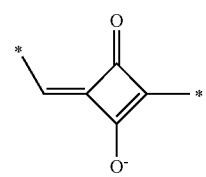

(A2-15)
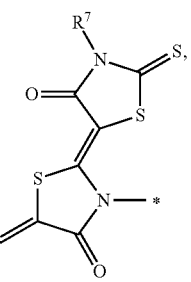

wherein X represents S, O, or NR, wherein R represents a hydrogen atom or an optionally substituted hydrocarbon group, and any hydrogen atom in the group may be substituted with a fluorine atom, a chlorine atom, a bromine atom, an iodine atom, a cyano group, a nitro group, an —OR$^7$ group, an —SR$^7$ group, an —NR$^7$R$^8$ group, or an optionally substituted aliphatic hydrocarbon group, wherein R$^7$ and R$^8$ each represent a hydrogen atom or an optionally substituted hydrocarbon group.

3. The dye-sensitized solar cell according to claim 2, wherein the structural formula (3) in the structural formula (2-1)

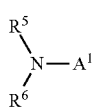   (3)

is any one of the following substructures (3-1) to (3-8), (3-1)
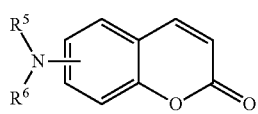

(3-2)
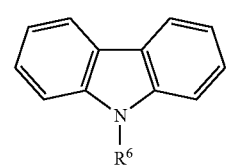

(3-3)
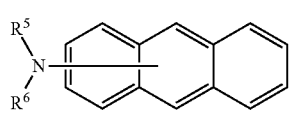

-continued (3-4)
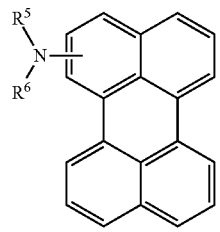

(3-5)
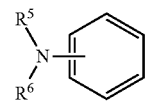

(3-6)
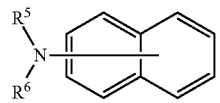

(3-7)
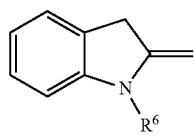

(3-8)
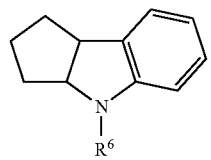

wherein A$^1$ is an optionally substituted aromatic hydrocarbon ring group or an optionally substituted aromatic heterocyclic group, and R$^5$ and R$^6$ each represent an optionally substituted hydrocarbon group, R$^5$ and R$^6$ may be linked together to form a ring, and R$^5$ and R$^6$ may be each independently linked with A$^1$ to form a ring, any hydrogen atoms in the formulae may be substituted with a fluorine atom, a chlorine atom, an iodine atom, a bromine atom, a cyano group, a nitro group, an —OR$^7$ group, an —SR$^7$ group, an optionally substituted aliphatic hydrocarbon group, or Y—SiR$^1$R$^2$R$^3$, wherein R$^1$, R$^2$, and R$^3$ each represent an optionally substituted hydrocarbon group or an optionally substituted hydrocarbonoxy group, and R$^7$ represents a hydrogen atom or an optionally substituted hydrocarbon group.

4. The dye-sensitized solar cell according to claim 1, wherein the basic compound is a pyridine derivative, an imidazole derivative, or a guanidine salt.

5. The dye-sensitized solar cell according to claim 1, wherein the electrolyte-containing layer is a layer containing a solvent, and the solvent contains at least 3-methoxypropionitrile, propylene carbonate, or 3-methyl-1-propylimidazolium iodide.

6. The dye-sensitized solar cell according to claim 1, wherein the oxide semiconductor layer comprises an oxide semiconductor which is titanium oxide or zinc oxide.

7. The dye-sensitized solar cell according to claim 2, wherein the basic compound is a pyridine derivative, an imidazole derivative, or a guanidine salt.

8. The dye-sensitized solar cell according to claim 3, wherein the basic compound is a pyridine derivative, an imidazole derivative, or a guanidine salt.

9. The dye-sensitized solar cell according to claim 2, wherein the electrolyte-containing layer is a layer containing a solvent, and the solvent contains at least 3-methoxypropionitrile, propylene carbonate, or 3-methyl-1-propylimidazolium iodide.

10. The dye-sensitized solar cell according to claim 3, wherein the electrolyte-containing layer is a layer containing a solvent, and the solvent contains at least 3-methoxypropionitrile, propylene carbonate, or 3-methyl-1-propylimidazolium iodide.

11. The dye-sensitized solar cell according to claim 4, wherein the electrolyte-containing layer is a layer containing a solvent, and the solvent contains at least 3-methoxypropionitrile, propylene carbonate, or 3-methyl-1-propylimidazolium iodide.

12. The dye-sensitized solar cell according to claim 2, wherein the oxide semiconductor layer comprises an oxide semiconductor which is titanium oxide or zinc oxide.

13. The dye-sensitized solar cell according to claim 3, wherein the oxide semiconductor layer comprises an oxide semiconductor which is titanium oxide or zinc oxide.

14. The dye-sensitized solar cell according to claim 4, wherein the oxide semiconductor layer comprises an oxide semiconductor which is titanium oxide or zinc oxide.

15. The dye-sensitized solar cell according to claim 5, wherein the oxide semiconductor layer comprises an oxide semiconductor which is titanium oxide or zinc oxide.

16. The dye-sensitized solar cell according to claim 7, wherein the electrolyte-containing layer is a layer containing a solvent, and the solvent contains at least 3-methoxypropionitrile, propylene carbonate, or 3-methyl-1-propylimidazolium iodide.

17. The dye-sensitized solar cell according to claim 8, wherein the electrolyte-containing layer is a layer containing a solvent, and the solvent contains at least 3-methoxypropionitrile, propylene carbonate, or 3-methyl-1-propylimidazolium iodide.

18. The dye-sensitized solar cell according to claim 7, wherein the oxide semiconductor layer comprises an oxide semiconductor which is titanium oxide or zinc oxide.

19. The dye-sensitized solar cell according to claim 8, wherein the oxide semiconductor layer comprises an oxide semiconductor which is titanium oxide or zinc oxide.

20. The dye-sensitized solar cell according to claim 9, wherein the oxide semiconductor layer comprises an oxide semiconductor which is titanium oxide or zinc oxide.

* * * * *